United States Patent
Cui et al.

(10) Patent No.: US 10,597,360 B2
(45) Date of Patent: Mar. 24, 2020

(54) PREPOLYMERS EXHIBITING RAPID DEVELOPMENT OF PHYSICAL PROPERTIES

(71) Applicant: PRC-DeSoto International, Inc., Sylmar, CA (US)

(72) Inventors: Weibin Cui, Rancho Palos Verdes, CA (US); Renhe Lin, Stevenson Ranch, CA (US)

(73) Assignee: PRC-DeSoto International, Inc., Sylmar, CA (US)

( * ) Notice: Subject to any disclaimer, the term of this patent is extended or adjusted under 35 U.S.C. 154(b) by 116 days.

(21) Appl. No.: 15/886,242

(22) Filed: Feb. 1, 2018

(65) Prior Publication Data

US 2018/0155280 A1    Jun. 7, 2018

Related U.S. Application Data

(62) Division of application No. 15/194,617, filed on Jun. 28, 2016, now Pat. No. 9,920,006.

(51) Int. Cl.

| C08G 75/02 | (2016.01) |
| C08G 75/12 | (2016.01) |
| C07C 323/12 | (2006.01) |
| C08G 75/045 | (2016.01) |
| C09K 3/10 | (2006.01) |

(52) U.S. Cl.
CPC ............ *C07C 323/12* (2013.01); *C08G 75/02* (2013.01); *C08G 75/045* (2013.01); *C08G 75/12* (2013.01); *C09K 3/1012* (2013.01); *C08G 2190/00* (2013.01); *C09K 2003/1059* (2013.01)

(58) Field of Classification Search
CPC ................................................. C08G 75/02

USPC ............................................................ 528/376
See application file for complete search history.

(56) References Cited

U.S. PATENT DOCUMENTS

| 4,366,307 A | 12/1982 | Singh et al. |
| 4,609,762 A | 9/1986 | Morris et al. |
| 4,623,711 A | 11/1986 | Morris et al. |
| 5,225,472 A | 7/1993 | Cameron et al. |
| 5,270,364 A | 12/1993 | Schwartz et al. |
| 5,284,888 A | 2/1994 | Morgan |
| 6,172,179 B1 | 1/2001 | Zook et al. |
| 6,509,418 B1 | 1/2003 | Zook et al. |
| 6,525,168 B2 | 2/2003 | Zook et al. |
| 7,009,032 B2 | 3/2006 | Bojkova et al. |

(Continued)

FOREIGN PATENT DOCUMENTS

WO    2008137199    11/2008

OTHER PUBLICATIONS

Non-Final Office Action for U.S. Appl. No. 15/194,617, dated Jun. 20, 2017, 8 pages.

(Continued)

*Primary Examiner* — Duc Truong
(74) *Attorney, Agent, or Firm* — William R. Lambert

(57) ABSTRACT

Hydroxyl-containing bis(alkenyl) ethers can be incorporated into the backbone of polythioether prepolymers and can be used as curing agents in thiol-terminated polythioether prepolymer compositions. Cured sealants prepared using compositions containing hydroxyl-containing bis(alkenyl) ether-containing polythioether prepolymers and/or hydroxyl-containing bis(alkenyl) ether curing agents exhibit improved physical properties such as rapid curing and compatibility with fillers suitable for use in aerospace sealant applications.

33 Claims, 2 Drawing Sheets

(56) References Cited

U.S. PATENT DOCUMENTS

| | | |
|---|---|---|
| 7,879,955 B2 | 2/2011 | Rao et al. |
| 8,138,273 B2 | 3/2012 | Rao et al. |
| 8,513,339 B1 | 8/2013 | Keledjian et al. |
| 8,871,896 B2 | 10/2014 | Anderson et al. |
| 8,952,124 B2 | 2/2015 | Rao et al. |
| 9,056,949 B2 | 6/2015 | Cai et al. |
| 9,062,139 B2 | 6/2015 | Rao et al. |
| 9,382,448 B2 | 7/2016 | Cai et al. |
| 9,650,552 B2 | 5/2017 | Cai et al. |
| 2004/0247792 A1 | 12/2004 | Sawant et al. |
| 2006/0175005 A1 | 8/2006 | Sawant et al. |
| 2010/0010133 A1 | 1/2010 | Zook et al. |
| 2010/0041839 A1 | 2/2010 | Anderson et al. |
| 2012/0234205 A1 | 9/2012 | Hobbs et al. |
| 2012/0238707 A1 | 9/2012 | Hobbs et al. |
| 2014/0051789 A1 | 2/2014 | Rao et al. |
| 2015/0240122 A1 | 8/2015 | Rao et al. |
| 2015/0240140 A1 | 8/2015 | Rao et al. |
| 2016/0257819 A1 | 9/2016 | Pathak et al. |

OTHER PUBLICATIONS

International Search Report and Written Opinion for PCT Application No. PCT/US2017/039818, dated Nov. 7, 2017, 7 pages.

PREPOLYMERS EXHIBITING RAPID DEVELOPMENT OF PHYSICAL PROPERTIES

This application is a divisional of U.S. application Ser. No. 15/194,617, filed on Jun. 28, 2016, now U.S. Pat. No. 9,920,006, which is incorporated by reference in its entirety.

FIELD

Hydroxyl-containing bis(alkenyl) ethers that can be incorporated into the backbone of polythioether prepolymers and can be used as curing agents in thiol-terminated polythioether prepolymer compositions are disclosed. Cured sealants prepared using compositions containing hydroxyl-containing bis(alkenyl) ether-containing polythioether prepolymers and/or hydroxyl-containing bis(alkenyl) ether curing agents exhibit improved physical properties such as rapid curing and filler compatibility suitable for use in aerospace sealant applications.

BACKGROUND

Sulfur-containing polythioether prepolymers are known to be useful in aerospace sealant applications. Polythioether prepolymers can be prepared by reacting a polythiol with a divinyl ether to provide prepolymers that provide sealants that meet the demanding performance requirements of the aerospace industry.

Among other requirements, aerospace sealants must be resistant to aerospace fluids including aviation fuel. Fuel resistance can be imparted to a sealant by including sulfur atoms in the backbone of the prepolymer. Divinyl ethers used to prepared polythioethers have not included sulfur atoms.

For certain aerospace sealant uses it can be desirable that the sealant cure rapidly following application to a surface.

For certain aerospace sealants it can also be desirable that the sealant contain a high loading of filler. Filler can be included in a sealant for a number of reasons such as to improve the physical properties of the cured sealant, to reduce the weight, to impart electrical conductivity, and/or to impart RFI/EMI shielding effectiveness. The addition of filler can increase the viscosity of the sealant, which can make the sealant difficult to apply. It can be desirable to reduce the viscosity of sealants containing fillers and especially those having a high filler content. Viscosity of compositions containing fillers can be reduced using plasticizers such as reactive diluents and lower molecular weight reactants. However, the addition of these additives can compromise the properties of the cured sealant.

Therefore, it is desirable to provide polythioether prepolymers that cure rapidly, exhibit improved fuel resistance, and for sealants having a high loading of filler particles, filler compatibility.

SUMMARY

According to the present invention, hydroxyl-containing bis(alkenyl) ethers of Formula (2) are provided:

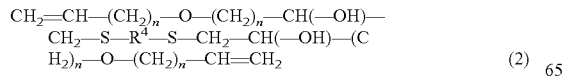

(2)

wherein,
each n is independently an integer from 1 to 4; and $R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or —[(—$CH_2$—)$_p$—X—]$_q$—(—$CH_2$—)$_r$—, wherein,
each X is independently selected from —O—, —S—, and —S—S—;
each p is independently an integer ranging from 2 to 6;
q is an integer from 1 to 5; and
r is an integer from 2 to 6.

According to the present invention, hydroxyl-containing bis(alkenyl) ethers are provided comprising reaction products of reactants comprising:

(a) a polythiol comprising a dithiol of Formula (6):

$$HS-R^4-SH \qquad (6)$$

wherein $R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or —[(—$CH_2$—)$_p$—X—]$_q$—(—$CH_2$—)$_r$—, wherein,
each X is independently selected from —O—, —S— and —S—S—;
each p is independently an integer from 2 to 6;
q is an integer from 1 to 5; and
r is an integer from 2 to 6; and (b) a compound of Formula (8):

(8)

wherein each n is independently an integer from 1 to 4.

According to the present invention, polythioether prepolymers are provided comprising a moiety of Formula (1):

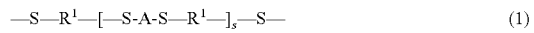

—S—$R^1$—[—S-A-S—$R^1$—]$_s$—S— (1)

wherein,
s is an integer from 1 to 60;
each A independently comprises a moiety of Formula (2a) or, a moiety of Formula (3a):

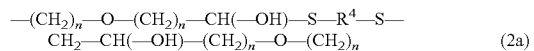

—($CH_2$)$_n$—O—($CH_2$)$_n$—CH(—OH)—S—$R^4$—S—
  $CH_2$—CH(—OH)—($CH_2$)$_n$—O—($CH_2$)$_n$ (2a)

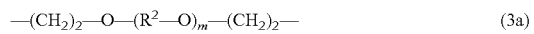

—($CH_2$)$_2$—O—($R^2$—O)$_m$—($CH_2$)$_2$— (3a)

wherein,
each n is independently an integer from 1 to 4;
each $R^1$ comprises $C_{2-10}$ alkanediyl, $C_{6-8}$ cycloalkanediyl, $C_{6-10}$ alkanecycloalkanediyl, or —[(—CHR—)$_p$—X—]$_q$—(CHR)$_r$—, wherein each R is independently selected from hydrogen and methyl, wherein,
each X is independently selected from —O— and —S—
each p is independently an integer from 2 to 6;
q is an integer from 1 to 5; and
r is an integer from 2 to 10;
m is 0 to 50; and
each $R^2$ comprises $C_{2-6}$ n-alkanediyl, $C_{3-6}$ branched alkanediyl, $C_{6-8}$ cycloalkanediyl, $C_{6-10}$ alkanecycloalkanediyl, or —[(—$CH_2$—)$_p$—O—]$_q$—(—$CH_2$—)$_r$, wherein,
each p is independently an integer ranging from 2 to 6;
q is an integer from 1 to 5; and
r is an integer from 2 to 10;

$R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-X-]_q-(-CH_2-)_r-$, wherein,
each X is independently selected from $-O-$, $-S-$ and $-S-S-$;
each p is an integer from 2 to 6;
q is an integer from 1 to 5; and
r is an integer from 2 to 6; and
at least one A comprises a moiety of Formula (2a).

According to the present invention, polythioether prepolymers are provided comprising reaction products of reactants comprising:

(a) a polythiol comprising a dithiol of Formula (6):

$$HS-R^1-SH \quad (6)$$

wherein,
$R^1$ comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_r-$, wherein:
each p is independently an integer from 2 to 6;
q is an integer from 1 to 5;
r is an integer from 2 to 10;
each R is independently selected from hydrogen and methyl; and
each X is independently selected from $-O-$, $-S-$, and $-NR^5-$, wherein $R^5$ is selected from hydrogen and methyl;

(b) a hydroxyl-containing bis(alkenyl) ether of Formula (2):

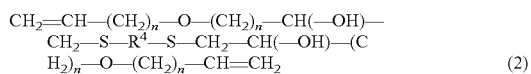

$$CH_2=CH-(CH_2)_n-O-(CH_2)_n-CH(-OH)-CH_2-S-R^4-S-CH_2-CH(-OH)-(CH_2)_n-O-(CH_2)_n-CH=CH_2 \quad (2)$$

wherein,
each n is independently an integer from 1 to 4;
$R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-X-]_q-(-CH_2-)_r-$, wherein,
each X is independently selected from $-O-$, $-S-$ and $-S-S-$;
each p is independently an integer from 2 to 6;
q is an integer from 1 to 5; and
r is an integer from 2 to 6; and (c) a divinyl ether of Formula (3):

$$CH_2=CH-O-(-R^2-O-)_m-CH=CH_2 \quad (3)$$

wherein,
m is 0 to 50; and
each $R^2$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-O-]_q-(-CH_2-)_r-$, wherein,
each p is independently an integer ranging from 2 to 6;
q is an integer from 1 to 5; and
r is an integer from 2 to 10.

According to the present invention, compositions comprising a hydroxyl-containing bis(alkenyl) ether-containing polythioether prepolymer of the present invention are provided.

According to the present invention, parts sealed with compositions comprising a hydroxyl-containing bis(alkenyl) ether-containing polythioether prepolymer of the present invention are provided.

According to the present invention, methods of sealing a part are provided comprising, applying compositions comprising a s hydroxyl-containing bis(alkenyl) ether-containing polythioether prepolymer of the present invention to a part; and curing the applied composition to seal the part.

BRIEF DESCRIPTION OF THE DRAWINGS

Those skilled in the art will understand that the drawings described herein are for illustration purposes only. The drawings are not intended to limit the scope of the present disclosure.

Figure 1:
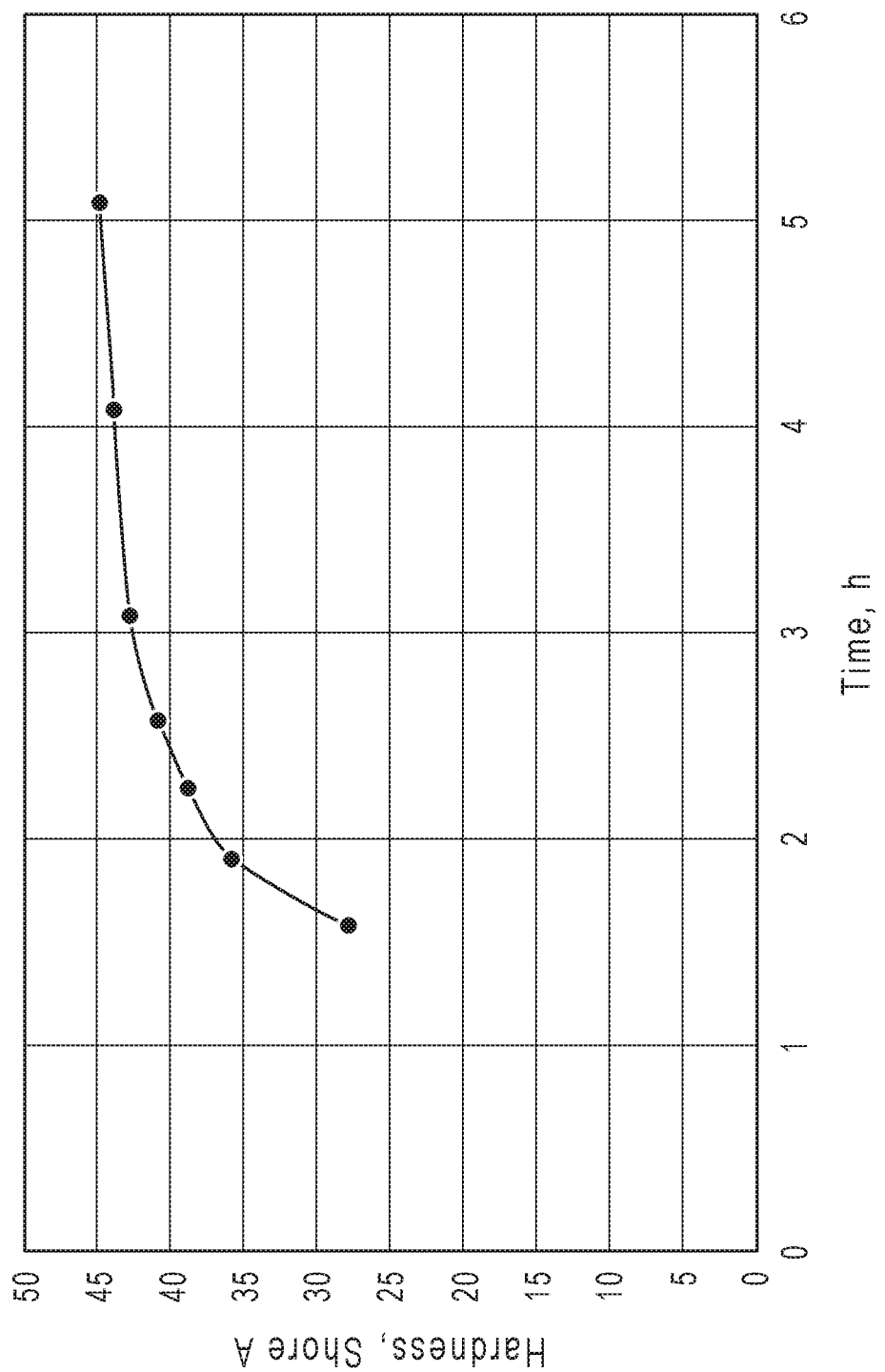
FIG. 1 is a graph showing the hardness of sealants during curing.

Reference is now made to certain compounds, compositions, and methods of the present invention. The disclosed compounds, compositions, and methods are not intended to be limiting of the claims. To the contrary, the claims are intended to cover all alternatives, modifications, and equivalents.

DETAILED DESCRIPTION

For purposes of the following description, it is to be understood that embodiments provided by the present disclosure may assume various alternative variations and step sequences, except where expressly specified to the contrary. Moreover, other than in the examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges encompassed therein. For example, a range of "1 to 10" is intended to include all sub-ranges between (and including) the recited minimum value of about 1 and the recited maximum value of about 10, that is, having a minimum value equal to or greater than about 1 and a maximum value of equal to or less than about 10. Also, in this application, the use of "or" means "and/or" unless specifically stated otherwise, even though "and/or" may be explicitly used in certain instances.

A dash ("—") that is not between two letters or symbols is used to indicate a point of bonding for a substituent or between two atoms. For example, $-CONH_2$ is bonded to another chemical moiety through the carbon atom.

"Alkanediyl" refers to a diradical of a saturated, branched or straight-chain, acyclic hydrocarbon group, having, for example, from 1 to 18 carbon atoms ($C_{1-18}$), from 1 to 14 carbon atoms ($C_{1-14}$), from 1 to 6 carbon atoms ($C_{1-6}$), from 1 to 4 carbon atoms ($C_{1-4}$), or from 1 to 3 hydrocarbon atoms ($C_{1-3}$). It will be appreciated that a branched alkanediyl has a minimum of three carbon atoms. An alkanediyl can be $C_{2-14}$ alkanediyl, $C_{2-10}$ alkanediyl, $C_{2-8}$ alkanediyl, $C_{2-6}$ alkanediyl, $C_{2-4}$ alkanediyl, or $C_{2-3}$ alkanediyl. Examples of alkanediyl groups include methane-diyl (—$CH_2$—), ethane-1,2-diyl (—$CH_2CH_2$—), propane-1,3-diyl and iso-propane-1,2-diyl (e.g., —$CH_2CH_2CH_2$— and —$CH(CH_3)CH_2$—), butane-1,4-diyl (—$CH_2CH_2CH_2CH_2$—), pentane-1,5-diyl (—$CH_2CH_2CH_2CH_2CH_2$—), hexane-1,6-diyl (—$CH_2CH_2CH_2CH_2CH_2CH_2$—), heptane-1,7-diyl, octane-1,8-diyl, nonane-1,9-diyl, decane-1,10-diyl, dodecane-1,12-diyl, and the like.

"Alkanecycloalkane" refers to a saturated hydrocarbon group having one or more cycloalkyl and/or cycloalkanediyl groups and one or more alkyl and/or alkanediyl groups, where cycloalkyl, cycloalkanediyl, alkyl, and alkanediyl are defined herein. Each cycloalkyl and/or cycloalkanediyl group(s) can be $C_{3-6}$, $C_{5-6}$, cyclohexyl or cyclohexanediyl. Each alkyl and/or alkanediyl group(s) can be $C_1$-6, $C_{1-4}$, $C_{1-3}$, methyl, methanediyl, ethyl, or ethane-1,2-diyl. An alkanecycloalkane group can be $C_{4-18}$ alkanecycloalkane, $C_{4-16}$ alkanecycloalkane, $C_{4-12}$ alkanecycloalkane, $C_{4-8}$ alkanecycloalkane, $C_{6-12}$ alkanecycloalkane, $C_{6-10}$ alkanecycloalkane, or $C_{6-9}$ alkanecycloalkane. Examples of alkanecycloalkane groups include 1,1,3,3-tetramethylcyclohexane and cyclohexylmethane.

"Alkanecycloalkanediyl" refers to a diradical of an alkanecycloalkane group. An alkanecycloalkanediyl group can be $C_{4-18}$ alkanecycloalkanediyl, $C_{4-16}$ alkanecycloalkanediyl, $C_{4-12}$ alkanecycloalkanediyl, $C_{4-8}$ alkanecycloalkanediyl, $C_{6-12}$ alkanecycloalkanediyl, $C_{6-10}$ alkanecycloalkanediyl, or $C_{6-9}$ alkanecycloalkanediyl. Examples of alkanecycloalkanediyl groups include 1,1,3,3-tetramethylcyclohexane-1,5-diyl and cyclohexylmethane-4,4'-diyl.

"Alkanearene" refers to a hydrocarbon group having one or more aryl and/or arenediyl groups and one or more alkyl and/or alkanediyl groups, where aryl, arenediyl, alkyl, and alkanediyl are defined here. Each aryl and/or arenediyl group(s) can be $C_{6-12}$, $C_{6-10}$, phenyl or benzenediyl. Each alkyl and/or alkanediyl group(s) can be $C_{1-6}$, $C_{1-4}$, $C_{1-3}$, methyl, methanediyl, ethyl, or ethane-1,2-diyl. An alkanearene group can be $C_{4-18}$ alkanearene, $C_{4-16}$ alkanearene, $C_{4-12}$ alkanearene, $C_{4-8}$ alkanearene, $C_{6-12}$ alkanearene, $C_{6-10}$ alkanearene, or $C_{6-9}$ alkanearene. Examples of alkanearene groups include diphenyl methane.

"Alkanearenediyl" refers to a diradical of an alkanearene group. An alkanearenediyl group is $C_{4-18}$ alkanearenediyl, $C_{4-16}$ alkanearenediyl, $C_{4-12}$ alkanearenediyl, $C_{4-8}$ alkanearenediyl, $C_{6-12}$ alkanearenediyl, $C_{6-10}$ alkanearenediyl, or $C_{6-9}$ alkanearenediyl. Examples of alkanearenediyl groups include diphenyl methane-4,4'-diyl.

"Alkenyl" group refers to a group $(R)_2C=C(R)_2$. An alkenyl group has the structure —$C(R)=C(R)_2$ where the alkenyl group is a terminal group and is bonded to a larger molecule. In such embodiments, each R may be selected from, for example, hydrogen and $C_{1-3}$ alkyl. Each R can be hydrogen and an alkenyl group can have the structure —$CH=CH_2$.

"Alkoxy" refers to a —OR group where R is alkyl as defined herein. Examples of alkoxy groups include methoxy, ethoxy, n-propoxy, isopropoxy, and n-butoxy. An alkoxy group can be $C_{1-8}$ alkoxy, $C_{1-6}$ alkoxy, $C_{1-4}$ alkoxy, or $C_{1-3}$ alkoxy.

"Alkyl" refers to a monoradical of a saturated, branched or straight-chain, acyclic hydrocarbon group having, for example, from 1 to 20 carbon atoms, from 1 to 10 carbon atoms, from 1 to 6 carbon atoms, from 1 to 4 carbon atoms, or from 1 to 3 carbon atoms. It will be appreciated that a branched alkyl has a minimum of three carbon atoms. An alkyl group can be $C_{2-6}$ alkyl, $C_{2-4}$ alkyl, or $C_{2-3}$ alkyl. Examples of alkyl groups include methyl, ethyl, n-propyl, iso-propyl, n-butyl, iso-butyl, tert-butyl, n-hexyl, n-decyl, and tetradecyl. An alkyl group can be $C_{2-6}$ alkyl, $C_{2-4}$ alkyl, or $C_{2-3}$ alkyl. It will be appreciated that a branched alkyl has at least three carbon atoms.

"Arenediyl" refers to diradical monocyclic or polycyclic aromatic group. Examples of arenediyl groups include benzene-diyl and naphthalene-diyl. An arenediyl group can be $C_{6-12}$ arenediyl, $C_{6-10}$ arenediyl, $C_{6-9}$ arenediyl, or benzene-diyl.

A "curable composition" refers to a composition that comprises at least two reactants capable of reacting to form a cured composition. For example, a curable composition can comprise a thiol-terminated polythioether prepolymer and a polyepoxide capable of reacting to form a cured polymer. A curable composition may include a catalyst for the curing reaction and other components such as, for example, fillers, pigments, and adhesion promoters. A curable composition may be curable at ambient conditions such as room temperature and humidity, or may require exposure to elevated temperature, moisture, or other condition(s) to initiate and/or to accelerate the curing reaction. A curable composition may initially be provided as a two-part composition including a separate base component and an accelerator component. The base composition can contain one of the reactants participating in the curing reaction such as a thiol-terminated polythioether prepolymer and the accelerator composition can contain the other reactant such as a polyepoxide. The two compositions can be mixed shortly before use to provide a curable composition. A curable composition can exhibit a viscosity suitable for a particular method of application. For example, a Class A sealant composition, which is suitable for brush-on applications, can be characterized by a viscosity from 1 poise to 500 poise. A Class B sealant composition, which is suitable for fillet seal applications, can be characterized by a viscosity from 4,500 poise to 20,000 poise. A Class C sealant composition, which is suitable for fay seal applications, can be characterized by a viscosity from 500 poise to 4,500 poise. After the two components of a sealant system are combined and mixed, the curing reaction can proceed and the viscosity of the curable composition can increase and at some point will no longer be workable. The period of time between when the two components are mixed to form the curable composition and when the curable composition can no longer be reasonably or practically applied to a surface for its intended purpose can be referred to as the working time. As can be appreciated, the working time can depend on a number of factors including, for example, the curing chemistry, the application method, and the temperature. The working time can also be referred to as the pot life. Once a curable composition is applied to a surface (and during application), the curing reaction can proceed to provide a cured composition. A cured composition develops a tack-free surfaces and fully cures over a period of time. A curable composition can be considered to be cured when the surface is tack-free, or can be considered cured, for example, when the Shore A hardness of the surface is 25 A for a Class C sealant and 30 A for a Class B sealant.

"Cycloalkanediyl" refers to a diradical saturated monocyclic or polycyclic hydrocarbon group. A cycloalkanediyl group can be $C_{3-12}$ cycloalkanediyl, $C_{3-8}$ cycloalkanediyl, $C_{3-6}$ cycloalkanediyl, or $C_{5-6}$ cycloalkanediyl. Examples of cycloalkanediyl groups include cyclohexane-1,4-diyl, cyclohexane-1,3-diyl and cyclohexane-1,2-diyl.

"Cycloalkyl" refers to a saturated monocyclic or polycyclic hydrocarbon mono-radical group. A cycloalkyl group can be $C_{3-12}$ cycloalkyl, $C_{3-8}$ cycloalkyl, $C_{3-6}$ cycloalkyl, or $C_{5-6}$ cycloalkyl.

"Heteroalkanediyl" refers to an alkanediyl group in which one or more of the carbon atoms are replaced with a heteroatom, such as N, O, S, or P. In a heteroalkanediyl, the one or more heteroatoms can be selected from N and O.

"Heterocycloalkanediyl" refers to a cycloalkanediyl group in which one or more of the carbon atoms are replaced with a heteroatom, such as N, O, S, or P. In a heterocycloalkanediyl, the one or more heteroatoms can be selected from N and O.

"Heteroarenediyl" refers to an arenediyl group in which one or more of the carbon atoms are replaced with a heteroatom, such as N, O, S, or P. In a heteroarenediyl, the one or more heteroatoms can be selected from N and O.

"Heterocycloalkanediyl" refers to a cycloalkanediyl group in which one or more of the carbon atoms are replaced with a heteroatom, such as N, O, S, or P. In a heterocycloalkanediyl, the one or more heteroatoms can be selected from N and O.

As used herein, "polymer" refers to oligomers, homopolymers, and copolymers. Unless stated otherwise, molecular weights are number average molecular weights for polymeric materials indicated as "Mn" as determined, for example, by end group analysis using iodine titration. A polymer also includes a prepolymer. A prepolymer such as a thiol-terminated polythioether prepolymer provided by the present disclosure can be combined with a curing agent to provide a curable composition, which can cure to provide a cured polymer network.

"Substituted" refers to a group in which one or more hydrogen atoms are each independently replaced with the same or different substituent(s). A substituent can be selected from halogen, —S(O)$_2$OH, —S(O)$_2$, —SH, —SR where R is $C_{1-6}$ alkyl, —COOH, —NO$_2$, —NR$_2$ where each R is independently selected from hydrogen and $C_{1-3}$ alkyl, —CN, =O, $C_{1-6}$ alkyl, —CF$_3$, —OH, phenyl, $C_{2-6}$ heteroalkyl, $C_{5-6}$ heteroaryl, $C_{1-6}$ alkoxy, and —COR where R is $C_{1-6}$ alkyl. A substituent can be —OH, —NH$_2$, or $C_{1-3}$ alkyl.

Hydroxyl-containing bis(alkenyl) ethers of the present invention include pendent hydroxyl groups and can include sulfur atoms.

Sealants prepared using hydroxyl-containing bis(alkenyl) ether-containing polythioethers having hydroxyl pendent groups can cure faster than sealants prepared using polythioethers without pendent hydroxyl groups in the backbone, and also exhibit lower viscosity in the presence of fillers.

Polythioether prepolymers provided by the present disclosure comprise hydroxyl-containing bis(alkenyl) ethers incorporated into the prepolymer backbone. A hydroxyl-containing bis(alkenyl) ether include hydroxyl pendent groups. Polythioether prepolymers provided by the present disclosure can be prepared by reacting a polythiol or combination of polythiols with a hydroxyl-containing bis(alkenyl) ether or combination of hydroxyl-containing bis(alkenyl) ethers.

Polythioether prepolymers provided by the present disclosure can be prepared by reacting a polythiol or combination of polythiols, a hydroxyl-containing bis(alkenyl) ether or combination of hydroxyl-containing bis(alkenyl) ethers, and a divinyl ether or combination of divinyl ethers. Divinyl ethers do not contain sulfur groups or hydroxyl pendent groups.

Polythioether prepolymers provided by the present disclosure can comprise a backbone of Formula (1):

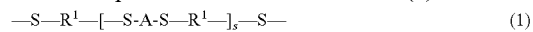

wherein,
s is an integer from 1 to 60;
each A comprises a moiety of Formula (2a), a moiety of Formula (3a), or a combination thereof:

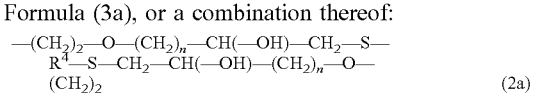

wherein,
each n is independently an integer from 1 to 4;
each $R^1$ comprises $C_{2-10}$ alkanediyl, $C_{6-8}$ cycloalkanediyl, $C_{6-10}$ alkanecycloalkanediyl, or —[(—CHR—)$_p$—X—]$_q$—(CHR)$_r$—, wherein each R is independently selected from hydrogen and methyl, wherein,
each X is independently selected from —O— and —S—;
each p is independently an integer from 2 to 6;
q is an integer from 1 to 5; and
r is an integer from 2 to 10;
m is an integer from 0 to 50; and
each $R^2$ comprises $C_{2-6}$ n-alkanediyl, $C_{3-6}$ branched alkanediyl, $C_{6-8}$ cycloalkanediyl, $C_{6-10}$ alkanecycloalkanediyl, or —[(—CH$_2$—)$_p$—O—]$_q$—(—CH$_2$—)$_r$, wherein,
each p is independently an integer ranging from 2 to 6;
q is an integer from 1 to 5; and
r is an integer from 2 to 10;
$R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or —[(—CH$_2$—)$_p$—X—]$_q$—(—CH$_2$—)$_r$—, wherein,
each X is independently selected from —O—, —S— and —S—S—;
each p is an integer from 2 to 6;
q is an integer from 1 to 5; and
r is an integer from 2 to 6; and
at least one A comprises a moiety of Formula (2a).

A moiety of Formula (2a) can be derived from a hydroxyl-containing bis(alkenyl) ether, such as a hydroxyl-containing bis(alkenyl) ether of Formula (2):

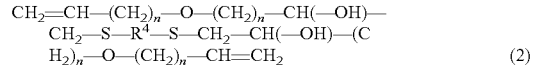

where n and $R^4$ are defined as in Formula (2a). A moiety of Formula (3a) can be derived from a divinyl ether, such as a divinyl ether of Formula (3):

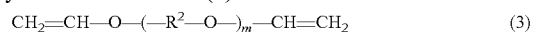

where m and $R^2$ are defined as in Formula (3a).

In polythioether prepolymers comprising a backbone of Formula (1), each A can be a moiety of Formula (2a).

In polythioether prepolymers comprising a backbone of Formula (1), each A can independently be a moiety of Formula (2a) or a moiety of Formula (3a), where at least one A is a moiety of Formula (2a).

In polythioether prepolymers comprising a backbone of Formula (1), each A can independently be a moiety of Formula (2a) or a moiety of Formula (3a).

In polythioether prepolymers comprising a backbone of Formula (1), each A can independently be a moiety of Formula (2a) or a moiety of Formula (3a), where at least one A is a moiety of Formula (2a).

In polythioether prepolymers comprising a backbone of Formula (1), from 20 mol % to 80 mol %, from 30 mol % to 70 mol %, or from 40 mol % to 60 mol % of the A moieties can comprise moieties of Formula (3a) and the remaining A moieties can be moieties of Formula (2a). For example, in a polythioether prepolymer of Formula (1) 50 mol % of the A moieties can comprise a moiety of Formula (3a) and 50 mol % of the A moieties can comprise a moiety of Formula (2a).

In polythioether prepolymers comprising a backbone of Formula (1), m can be, for example, an integer from 1 to 40, from 1 to 20, from 2 to 60, from 2 to 40, from 2 to 20, from 5 to 60, from 5 to 40, from 5 to 20, from 10 to 40, or from 10 to 30.

Polythioether prepolymers comprising a backbone having the structure of Formula (1) can be terminated, for example, in a thiol, hydroxyl, isocyanate, alkenyl, epoxy, polyalkoxysilyl, or Michael acceptor group. A terminal functional group can be selected as suitable for a particular curing chemistry.

Polythioether prepolymers comprising a backbone having the structure of Formula (1) can be difunctional, can have a functionality from 3 to 6, or can be characterized by an average non-integer functionality reflecting a combination of polythioether prepolymers having different functionalities.

Polythioether prepolymers comprising a backbone having the structure of Formula (1) can include a combination of polythioether prepolymers having different functionalities such as a combination of difunctional polythioether prepolymers and polythioether prepolymers having a functionality from 3 to 6. A polythioether prepolymer can include a combination of difunctional polythioether prepolymers and trifunctional polythioether prepolymers.

Polythioether prepolymers can comprise difunctional polythioether prepolymers of Formula (1a), a polyfunctional polythioether prepolymer of Formula (1b), or a combination thereof:

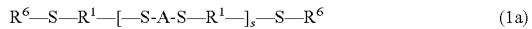

$$R^6—S—R^1—[—S-A-S—R^1—]_s—S—R^6 \quad (1a)$$

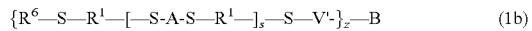

$$\{R^6—S—R^1—[—S-A-S—R^1—]_s—S—V'-\}_z—B \quad (1b)$$

wherein,
s, $R^1$, and A are defined as in Formula (1);
each $R^6$ is hydrogen or is a moiety comprising a terminal functional group; and
B represents a core of a z-valent polyfunctionalizing agent $B(—V)_z$ wherein:
z is an integer from 3 to 6; and
each V is a moiety comprising a terminal group reactive with a thiol group; and
each —V'— is derived from the reaction of —V with a thiol.

In polythioether prepolymers of Formula (1a) and (1b), each $R^6$ can be hydrogen and a polythioether prepolymer comprises a thiol-terminated polythioether prepolymer of Formula (1c), a thiol-terminated polythioether prepolymer of Formula (1d), or a combination thereof:

$$HS—R^1—[—S-A-S—R^1—]_s—SH \quad (1c)$$

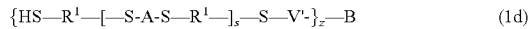

$$\{HS—R^1—[—S-A-S—R^1—]_s—S—V'-\}_z—B \quad (1d)$$

where s, $R^1$, A, B, z, and V' are defined as for Formula (1a) and Formula (1b); and at least one A comprises a moiety of Formula (2b)

In polythioether prepolymers of Formula (1a) and (1b), a terminal functional group of $R^6$ can comprise a thiol, hydroxyl, isocyanate, alkenyl, epoxy, polyalkoxysilyl, or a Michael acceptor group.

Thiol-terminated polythioethers can be prepared, for example, using the methods described in U.S. Pat. No. 6,172,179, which is incorporated by reference in its entirety.

Polythiols, hydroxyl-containing bis(alkenyl) ethers, and divinyl ethers can be reacted in relative amounts such that the molar ratio of thiol groups to alkenyl groups is greater than 1:1, such as from 1.1:1.0 to 2.0:1.0. The reaction between the polythiols, hydroxyl-containing (bis)alkenyl ethers, and divinyl ethers may be catalyzed by a free radical catalyst. Suitable free radical catalysts include, for example, azo compounds, for example azobisnitriles such as azo(bis) isobutyronitrile (AIBN); organic peroxides such as benzoyl peroxide and t-butyl peroxide; and inorganic peroxides such as hydrogen peroxide. The catalyst may be, for example, a free-radical catalyst, an ionic catalyst, or ultraviolet radiation. A catalyst may not comprise an acidic or basic compound, and may not produce acidic or basic compounds upon decomposition. Examples of free-radical catalysts include azo-type catalyst, such as Vazo®-57 (Du Pont), Vazo®-64 (Du Pont), Vazo®-67 (Du Pont), V-70® (Wako Specialty Chemicals), and V-65B® (Wako Specialty Chemicals). Examples of other free-radical catalysts include alkyl peroxides, such as t-butyl peroxide. The reaction may also be effected by irradiation with ultraviolet light either with or without a cationic photoinitiating moiety. Thiol-terminated polythioether prepolymers provided by the present disclosure may be prepared by combining at least one polythiol at least one hydroxyl-containing bis(alkenyl) ether, and optionally at least one divinyl ether followed by addition of an appropriate catalyst, and carrying out the reaction at a temperature from 30° C. to 120° C., such as 70° C. to 90° C., for a time from 2 hours to 24 hours, such as from 2 hours to 6 hours.

Polythioether prepolymers of Formula (1a) and Formula (1b) in which each $R^6$ comprises a terminal functional group can be referred to as terminal-modified polythioether prepolymers. Terminal-modified polythioether prepolymers can be obtained by first preparing a thiol-terminated polythioether prepolymer of Formula (1c) and/or Formula (1d), and then reacting the terminal thiol groups of the thiol-terminated prepolymer with a compound comprising a moiety reactive with thiol groups and a desired terminal functional group. Examples of groups reactive with thiol groups include alkenyl, isocyanate, epoxy, and Michael acceptor groups. Examples of suitable terminal functional groups include alkenyl groups, isocyanate groups, epoxy groups, polyalkoxysilyl groups, hydroxyl groups, amino groups, and Michael acceptor groups.

For example, modified polythioether prepolymers of Formula (1a) and/or Formula (1b) in which $R^6$ comprises an epoxy group can be prepared, for example, by reacting thiol-terminated polythioether prepolymers of Formula (1c) and/or Formula (1d) with a compound having an epoxy group (—CH(—O—CH$_2$—)) and a group reactive with thiol groups such as a monoepoxide of Formula (4):

$$R^8—R^9—\overset{O}{\underset{}{\triangleleft}} \quad (4)$$

where $R^8$ comprises a group, other than an epoxy group that is reactive with a thiol group. $R^8$ can be derived from an alkenyl group or an olefin conjugated with an electron attracting group such as acrylates methacrylates, acrylonitrile and methacrylonitrile. $R^9$ can be selected from a $C_{2-10}$ alkanediyl group, and a $C_{2-10}$ alkyleneoxy group. For example, an epoxy-modified polythioether prepolymer of Formula (1a) and/or Formula (1b) can be prepared by reacting a thiol-terminated polythioether prepolymer of Formula (1c) and/or Formula (1d) with a monoepoxide such as allyl glycidyl ether to provide the corresponding epoxy-terminated modified polythioether prepolymer of Formula (1a) and/or Formula (1b).

For example, modified polythioether prepolymers of Formula (1a) and/or Formula (1b) in which $R^6$ comprises a hydroxyl group can be prepared by reacting thiol-terminated polythioether prepolymers of Formula (1c) and/or Formula (1d) with a hydroxyl vinyl ether. Hydroxyl vinyl ethers can be used to functionalize a thiol-terminated sulfur-containing prepolymer with a group reactive with an isocyanate group. A hydroxyl-functional vinyl ether can have the structure of Formula (5):

$$CH_2=CH-O-(CH_2)_t-OH \quad (5)$$

where t is an integer from 2 to 10. In hydroxyl-functional vinyl ethers of Formula (5), t can be 1, 2, 3, 4, 5, or t can be 6. Examples of suitable hydroxyl-functional vinyl ethers useful for reacting with thiol-terminated sulfur-containing prepolymers include 1,4-cyclohexane dimethylol monovinyl ether, 1-methyl-3-hydroxypropyl vinyl ether, 4-hydroxybutyl vinyl ether, and a combination of any of the foregoing. A hydroxyl-functional vinyl ether can be 4-hydroxybutyl vinyl ether.

For example, modified polythioether prepolymers of Formula (1a) and/or Formula (1b) in which $R^6$ is an isocyanate group can be prepared by reacting a hydroxyl modified thiol-terminated polythioether prepolymer of Formula (1c) and/or Formula (1d) with a polyisocyanate. A polyisocyanate can be difunctional, n-functional where n is an integer from 3 to 6, or a combination of any of the foregoing. A polyisocyanate can be difunctional and can be referred to as a diisocyanate. A diisocyanate may be aliphatic, alicyclic, or aromatic.

Examples of suitable aliphatic diisocyanates include, 1,6-hexamethylene diisocyanate, 1,5-diisocyanato-2-methyl-pentane, methyl-2,6-diisocyanatohexanoate, bis(isocyanatomethyl)cyclohexane, 1,3-bis(isocyanatomethyl)cyclohexane, 2,2,4-trimethylhexane 1,6-diisocyanate, 2,4,4-trimethylhexane 1,6-diisocyanate, 2,5(6)-bis(isocyanatomethyl)cyclo[2.2.1]heptane, 1,3,3-trimethyl-1-(isocyanatomethyl)-5-isocyanatocyclohexane, 1,8-diisocyanato-2,4-dimethyloctane, octahydro-4,7-methano-1H-indenedimethyl diisocyanate, and 1,1'-methylenebis(4-isocyanatocyclohexane), and 4,4-methylene dicyclohexyl diisocyanate) ($H_{12}$MDI). Examples of suitable aromatic diisocyanates include 1,3-phenylene diisocyanate, 1,4-phenylene diisocyanate, 2,6-toluene diisocyanate (2,6-TDI), 2,4-toluene diisocyanate (2,4-TDI), a blend of 2,4-TDI and 2,6-TDI, 1,5-diisocyanatonaphthalene, diphenyl oxide 4,4'-diisocyanate, 4,4'-methylenediphenyl diisocyanate (4,4-MDI), 2,4'-methylenediphenyl diisocyanate (2,4-MDI), 2,2'-diisocyanatodiphenylmethane (2,2-MDI), diphenylmethane diisocyanate (MDI), 3,3'-dimethyl-4,4'-biphenylene isocyanate, 3,3'-dimethoxy-4,4'-biphenylene diisocyanate, 1-[(2,4-diisocyanatophenyl)methyl]-3-isocyanato-2-methyl benzene, and 2,4,6-triisopropyl-m-phenylene diisocyanate.

Examples of suitable alicyclic diisocyanates from which the diisocyanates may be selected include isophorone diisocyanate, cyclohexane diisocyanate, methylcyclohexane diisocyanate, bis(isocyanatomethyl)cyclohexane, bis(isocyanatocyclohexyl)methane, bis(isocyanatocyclohexyl)-2,2-propane, bis(isocyanatocyclohexyl)-1,2-ethane, 2-isocyanatomethyl-3-(3-isocyanatopropyl)-5-isocyanatomethyl-bicyclo[2.2.1]-heptane, 2-isocyanatomethyl-3-(3-isocyanatopropyl)-6-isocyanatomethyl-bicyclo[2.2.1]-heptane, 2-isocyanatomethyl-2-(3-isocyanatopropyl)-5-isocyanatomethyl-bicyclo[2.2.1]-heptane, 2-isocyanatomethyl-2-(3-isocyanatopropyl)-6-isocyanatomethyl-bicyclo[2.2.1]-heptane, 2-isocyanatomethyl-3-(3-isocyanatopropyl)-6-(2-isocyanatoethyl)-bicyclo[2.2.1]-heptane, 2-isocyanatomethyl-2-(3-isocyanatopropyl)-5-(2-isocyanatoethyl)-bicyclo[2.2.1]-heptane, and 2-isocyanatomethyl-2-(3-isocyanatopropyl)-6-(2-isocyanatoethyl)-bicyclo[2.2.1]-heptane.

Examples of suitable aromatic diisocyanates in which the isocyanate groups are not bonded directly to the aromatic ring include, but are not limited to, bis(isocyanatoethyl)benzene, α,α,α',α'-tetramethylxylene diisocyanate, 1,3-bis(1-isocyanato-1-methylethyl)benzene, bis(isocyanatobutyl)benzene, bis(isocyanatomethyl)naphthalene, bis(isocyanatomethyl)diphenyl ether, bis(isocyanatoethyl)phthalate, and 2,5-di(isocyanatomethyl)furan. Aromatic diisocyanates having isocyanate groups bonded directly to the aromatic ring include phenylene diisocyanate, ethylphenylene diisocyanate, isopropylphenylene diisocyanate, dimethylphenylene diisocyanate, diethylphenylene diisocyanate, diisopropylphenylene diisocyanate, naphthalene diisocyanate, methylnaphthalene diisocyanate, biphenyl diisocyanate, 4,4'-diphenylmethane diisocyanate, bis(3-methyl-4-isocyanatophenyl)methane, bis(isocyanatophenyl)ethylene, 3,3'-dimethoxy-biphenyl-4,4'-diisocyanate, diphenylether diisocyanate, bis(isocyanatophenylether)ethyleneglycol, bis(isocyanatophenylether)-1,3-propyleneglycol, benzophenone diisocyanate, carbazole diisocyanate, ethylcarbazole diisocyanate, dichlorocarbazole diisocyanate, 4,4'-diphenylmethane diisocyanate, p-phenylene diisocyanate, 2,4-toluene diisocyanate, and 2,6-toluene diisocyanate.

Isocyanate-terminated polythioether prepolymers may be synthesized by reacting, for example, a diisocyanate with an appropriately terminated hydroxyl-containing bis(alkenyl) ether-containing polythioether such as, for example, a hydroxyl-terminated polythioether, at a suitable temperature such as from 50° C. to 100° C. for a suitable time such as from 1 hour to 4 hours, in the presence of a tin catalyst, such as dibutyltin dilaurate.

For example, modified polythioether prepolymers of Formula (1a) and/or Formula (1b) in which $R^6$ comprises a alkenyl group can be prepared by reacting thiol-terminated polythioether prepolymers of Formula (1c) and/or Formula (1d) with a divinyl ether or a hydroxyl-containing bis(alkenyl) ether provided by the present disclosure.

For example, modified polythioether prepolymers of Formula (1a) and/or Formula (1b) in which $R^6$ comprises a polyalkoxysilyl group can be prepared by reacting thiol-terminated polythioether prepolymers of Formula (1c) and/or Formula (1d) with an isocyanatoalkyltrialkoxysilane such as a 3-isocyanatopropyltrimethoxysilane or 3-isocyanatopropyltriethoxysilane in the presence of dibutyltin dilaurate to provide the corresponding polyalkoxysilyl-terminated modified polythioether prepolymer of Formula (1a) and/or Formula (1b).

For example, modified polythioether prepolymers of Formula (1a) and/or Formula (1b) in which $R^6$ comprises an amino group can be prepared by reacting thiol-terminated polythioether prepolymers of Formula (1c) and/or Formula (1d) with a monofunctional 4-amino butyl vinyl ether with a free-radical initiator. Alternatively, an amino-terminated polythioether may be obtained by reacting an isocyanate-terminated polythioether with a diamine such as 4-(aminomethyl)aniline to provide the corresponding amino-terminated polythioether prepolymer. Amino-terminated polythioether prepolymers may also be obtained by reacting a thiol-terminated polythioether prepolymer with an amino-substituted benzoate such as ethyl-4-aminobenzoate in the presence of $Bu_2SnO$ or NaOMe at elevated temperature to provide the corresponding amino-terminated polythioether prepolymer.

For example, modified polythioether prepolymers of Formula (1a) and/or Formula (1b) in which $R^6$ comprises a Michael acceptor group can be prepared by reacting thiol-terminated polythioether prepolymers of Formula (1c) and/or Formula (1d) with a compound having a terminal Michael acceptor group and a group reactive with thiol groups such as a divinylsulfone, in the presence of an amine catalyst. Michael acceptor/polythioether chemistries and compounds are disclosed in U.S. Pat. No. 8,871,896, which is incorporated by reference in its entirety.

Polythioether prepolymers provided by the present disclosure can comprise reaction products of reactants comprising a polythiol or a combination of polythiols and a hydroxyl-containing bis(alkenyl) ether or a combination of hydroxyl-containing bis(alkenyl) ethers. Such prepolymers include polythioether prepolymers comprising a backbone having the structure of Formula (1) in which each A comprises a moiety of Formula (2a).

For example, polythioether prepolymers provided by the present disclosure can comprise reaction products of reactants comprising:

(a) a polythiol comprising a dithiol of Formula (6):

where,
each $R^1$ comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_r-$, wherein:
  each p is independently an integer from 2 to 6;
  q is an integer from 1 to 5;
  r is an integer from 2 to 10;
  each R is independently selected from hydrogen and methyl; and
  each X is independently selected from $-O-$, $-S-$, and $-NR^5-$, wherein $R^5$ is selected from hydrogen and methyl; and (b) a hydroxyl-containing bis(alkenyl) ether of Formula (2):

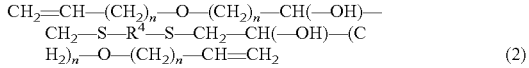

wherein,
each n is independently an integer from 1 to 4; and
$R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-X-]_q-(-CH_2-)_r-$, wherein,
  each X is independently selected from $-O-$, $-S-$ and $-S-S-$;
  each p is independently an integer from 2 to 6;
  q is an integer from 1 to 5; and
  r is an integer from 2 to 6.

A polythiol can comprise a dithiol, a polythiol having a thiol functionality from 3 to 6, or a combination of a dithiol and a polythiol having a thiol functionality from 3 to 6.

For example, in addition to a polythiol of Formula (6) and a hydroxyl-containing bis(alkenyl) ether of Formula (2), reactants used to prepare a polythioether prepolymer provided by the present disclosure can further include a polythiol of Formula (7):

wherein,
B comprises a core of a z-valent polyfunctionalizing agent $B(-V)_z$;
z is an integer from 3 to 6; and
each $-V$ is independently a moiety comprising a terminal alkenyl group or a terminal thiol group.

In polyfunctionalizing agents having the structure of Formula (7), z can be 3, 4, 5, or 6.

In polyfunctionalizing agents having the structure of Formula (7), each V can comprise a terminal alkenyl group. In polyfunctionalizing agents having the structure of Formula (7), each V can comprise a terminal thiol group. Polyfunctionalizing agents suitable for preparing polyfunctional thiol-terminated polythioether prepolymers can include trifunctionalizing agents, that is, compounds where z is 3. Suitable trifunctionalizing agents include, for example, triallyl cyanurate (TAC), 1,2,3-propanetrithiol, isocyanurate-containing trithiols, and combinations thereof, as disclosed in U.S. Application Publication No. 2010/0010133. Other useful polyfunctionalizing agents include trimethylolpropane trivinyl ether, and the polythiols described in U.S. Pat. Nos. 4,366,307; 4,609,762; and 5,225,472. Mixtures of polyfunctionalizing agents may also be used.

Polythioether prepolymers provided by the present disclosure can comprise a hydroxyl-containing bis(alkenyl) ether incorporated into the prepolymer backbone.

Polythioether prepolymers provided by the present disclosure can comprise reaction products of reactants comprising a polythiol or a combination of polythiols and a hydroxyl-containing bis(alkenyl) ether or a combination of hydroxyl-containing bis(alkenyl) ethers.

Polythioether prepolymers provided by the present disclosure can comprise reaction products of reactants comprising a polythiol or a combination of polythiols, a hydroxyl-containing bis(alkenyl) ether or a combination of hydroxyl-containing bis(alkenyl) ethers, and a divinyl ether or combination of divinyl ethers.

A polythiol can comprise a dithiol, a polythiol having a thiol functionality from 3 to 6, or a combination of a dithiol and a polythiol having a thiol functionality from 3 to 6.

Polythioether prepolymers provided by the present disclosure can comprise reaction products of reactants comprising:

(a) a polythiol comprising a dithiol of Formula (6):

wherein each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_p-$, wherein,
  each p is independently an integer from 2 to 6;
  q is an integer from 1 to 5;
  r is an integer from 2 to 10;
  each R is independently selected from hydrogen and methyl; and
  each X is independently selected from $-O-$, $-S-$, and $-NR^5-$, wherein $R^5$ is selected from hydrogen and methyl;

(b) a hydroxyl-containing bis(alkenyl) ether of Formula (2):

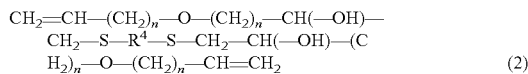

$$CH_2=CH-(CH_2)_n-O-(CH_2)_n-CH(-OH)-CH_2-S-R^4-S-CH_2-CH(-OH)-(CH_2)_n-O-(CH_2)_n-CH=CH_2 \quad (2)$$

wherein,
  each n is independently an integer from 1 to 4; and
  $R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-X-]_q-(-CH_2-)_r-$, wherein,
    each X is independently selected from $-O-$ and $-S-$;
    each p is independently an integer ranging from 2 to 6;
    q is an integer from 1 to 5; and
    r is an integer from 2 to 6.

Polythioether prepolymers provided by the present disclosure can comprise reaction products of reactants comprising:

(a) a polythiol comprising a dithiol of Formula (6):

$$HS-R^1-SH \quad (6)$$

wherein each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_p-$, wherein,
  each p is independently an integer from 2 to 6;
  q is an integer from 1 to 5;
  r is an integer from 2 to 10;
  each R is independently selected from hydrogen and methyl; and
  each X is independently selected from $-O-$, $-S-$, and $-NR^5-$, wherein $R^5$ is selected from hydrogen and methyl;

(b) a hydroxyl-containing bis(alkenyl) ether of Formula (2):

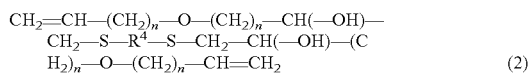

$$CH_2=CH-(CH_2)_n-O-(CH_2)_n-CH(-OH)-CH_2-S-R^4-S-CH_2-CH(-OH)-(CH_2)_n-O-(CH_2)_n-CH=CH_2 \quad (2)$$

wherein,
  each n is independently an integer from 1 to 4; and
  $R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)-X-]_q-(-CH_2-)_r-$, wherein,
    each X is independently selected from $-O-$ and $-S-$;
    each p is independently an integer ranging from 2 to 6;
    q is an integer from 1 to 5; and
    r is an integer from 2 to 6; and (c) a divinyl ether of Formula (3):

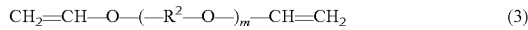

$$CH_2=CH-O-(-R^2-O-)_m-CH=CH_2 \quad (3)$$

wherein,
  m is 0 to 50; and
  each $R^2$ independently comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-O-]_q-(-CH_2-)_r-$, wherein,
    p is an integer ranging from 2 to 6;
    q is an integer from 1 to 5; and
    r is an integer from 2 to 10.

A dithiol and a hydroxyl-containing bis(alkenyl) ether can include any of those disclosed herein.

A reactant can further comprise a polyfunctionalizing agent of Formula (7):

$$B(-V)_z \quad (7)$$

wherein,
  B represents a core of a z-valent polyfunctionalizing agent $B(-V)_z$,
  z is an integer from 3 to 6; and
  each $-V$ is a moiety comprising terminal thiol group or a terminal alkenyl group.

Polyfunctionalizing agents of Formula (7) can also be referred to as thiol-terminated polyfunctionalizing agents. Examples of suitable polythiols of Formula (7) include 1,2,3-propane trithiol.

Polyalkenyl compounds of Formula (7) can also be referred to as alkenyl-terminated polyfunctionalizing agents. Examples of suitable polyalkenyl functionalizing agents of Formula (7) include TAC. A polyalkenyl functionalizing agent can include a multifunctional hydroxyl-containing bis(alkenyl) ether provided by the present disclosure.

The reactants can include an approximately stoichiometric ratio of thiol groups to alkenyl groups.

The thiol groups can include those derived from the polythiols including a dithiol and thiol-terminated polyfunctionalizing agent.

The alkenyl component of the reactants include the hydroxyl-containing bis(alkenyl) ether, the divinyl ether, and an alkenyl-terminated polyfunctionalizing agent. The alkenyl component can include from 20 mol % to 80 mol % of the hydroxyl-containing bis(alkenyl) ether with the remainder being the divinyl ether. For example, the alkenyl component can comprise 40 mol % of the hydroxyl-containing bis(alkenyl) ether and 60 mol % of the divinyl ether. The alkenyl component can comprise from 30 mol % to 70 mol %, from 40 mol % to 60 mol %, or from 45 mol % to 55 mol % of the hydroxyl-containing bis(alkenyl) ether with the remainder being the divinyl ether.

The reactants can be reacted in the presence of a suitable catalyst at elevated temperature to provide a hydroxyl-containing bis(alkenyl) ether-containing polythioether prepolymer.

Examples of suitable catalysts include a tertiary amine catalyst. Examples of suitable tertiary-amine catalysts include N,N-dimethylethanolamine (DMEA), triethylene diamine (TEDA), bis(2-dimethylaminoethyl)ether (BDMEE), N-ethylmorpholine, N',N'-dimethylpiperazine, N,N,N',N',N'-pentamethyl-diethylene-triamine (PMDETA), N,N-dimethylcyclohexylamine (DMCHA), N,N-dimethylbenzylamine (DMBA), N,N-dimethylcethylamine, N,N,N',N'',N'''-pentamethyl-dipropylene-triamine (PMDPTA), triethylamine, 1-(2-hydroxypropyl)imidazole, 1,8-diazabicyclo[5.4.0]undec-7-ene bicarbonate (DBU), 1,4-diazabicyclo[2.2.2]octane (DABCO®) such as DABCO® 33-LV (Air Products and Chemicals).

In dithiols of Formula (6), $R^1$ can be $C_{2-6}$ n-alkanediyl, such as ethane-diyl, n-propane-diyl, n-butane-diyl, n-pentane-diyl, or n-hexane-diyl.

In dithiols of Formula (6), $R^1$ can be $-[(-CHR-)_p-X-]_q-(-CHR-)_r-$.

In dithiols of Formula (6), $R^1$ can be $-[(-CHR-)_p-X-]_q-(-CHR-)_r-$, where at least one R can be $-CH_3$.

In dithiols of Formula (6), $R^1$ can be $-[(-CH_2-)_p-X-]_q-(-CH_2-)_r-$.

In dithiols of Formula (6), $R^1$ can be $-[(-CH_2-)_p-X-]_q-(-CH_2-)_r-$, and each X can be $-O-$.

In dithiols of Formula (6), $R^1$ can be $-[(-CH_2-)_p-X-]_q-(-CH_2-)_r-$, and each X can be $-S-$.

In dithiols of Formula (6), $R^1$ can be $-[(-CH_2-)_p-X-]_q-(-CH_2-)_r-$, and each p can be 2 and r can be 2.

In dithiols of Formula (6), $R^1$ can be $-[(-CH_2-)_p-X-]_q-(-CH_2-)_r-$, where p can be 1, 2, 3, 4, or 5.

In dithiols of Formula (6), $R^1$ can be $-[(-CH_2-)_p-X-]_q-(-CH_2-)_r-$, where q can be 1, 2, 3, 4, or 5.

In dithiols of Formula (6), $R^1$ can be $-[(-CH_2-)_p-X-]_q-(-CH_2-)_r-$, where r can be 1, 2, 3, 4, or 5.

In dithiols of Formula (6), $R^1$ can be $-[(-CH_2-)_p-X-]_q-(-CH_2-)_r-$, where each p can be 2 and r can be 2; and q can be 1, 2, 3, 4, or 5.

In dithiols of Formula (6), $R^1$ can be $-[(-CH_2-)_p-X-]_q-(-CH_2-)_r-$, where each X can be $-S-$; each p can be 2 and r can be 2; and q can be 1, 2, 3, 4, or 5.

In dithiols of Formula (6), $R^1$ can be $-[(-CH_2-)_p-X-]_q-(-CH_2-)_r-$, where each X can be $-O-$; each p can be 2 and r can be 2; and q can be 1, 2, 3, 4, or 5.

Examples of suitable dithiols include dimercaptodiethylsulfide (DMDS) (in Formula (6), $R^1$ is $-[(-CH_2-)_p-X-]_q-(CH_2)_r-$, where p is 2, r is 2, q is 1, and X is $-S-$); dimercaptodioxaoctane (DMDO) (in Formula (6), $R^1$ is $-[(-CH_2-)_p-X-]_q-(CH_2)_r-$, wherein p is 2, q is 2, r is 2, and X is $-O-$); and 1,5-dimercapto-3-oxapentane (in Formula (6), $R^1$ is $-[(-CH_2-)_p-X-]_q-(CH_2)_r-$, wherein p is 2, r is 2, q is 1, and X is $-O-$).

Other examples of suitable dithiols of Formula (6) include 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide, methyl-substituted dimercaptodiethylsulfide, dimethyl-substituted dimercaptodiethylsulfide, dimercaptodioxaoctane, 1,5-dimercapto-3-oxapentane, and a combination of any of the foregoing. A dithiol may have one or more pendent groups selected from a lower (e.g., $C_{1-6}$) alkyl group, a lower alkoxy group, and a hydroxyl group. Suitable alkyl pendent groups include, for example, $C_{1-6}$ linear alkyl, $C_{3-6}$ branched alkyl, cyclopentyl, and cyclohexyl.

Examples of dithiols having pendent methyl groups include, methyl-substituted DMDS, such as $HS-CH_2CH(-CH_3)-S-CH_2CH_2-SH$, $HS-CH(-CH_3)CH_2-S-CH_2CH_2-SH$ and dimethyl substituted DMDS, such as $HS-CH_2CH(-CH_3)-S-CHCH_3CH_2-SH$ and $HS-CH(-CH_3)CH_2-S-CH_2CH(-CH_3)-SH$.

Hydroxyl-containing bis(alkenyl) ethers provided by the present disclosure can have the structure of Formula (2):

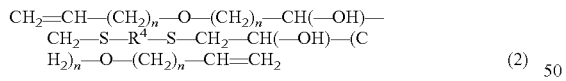     (2)

wherein,
each n is independently an integer from 1 to 4; and
$R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-X-]_q-(-CH_2-)_r-$, wherein,
each X is independently selected from $-O-$, $-S-$, and $-S-S-$;
each p is independently an integer ranging from 2 to 6;
q is an integer from 1 to 5; and
r is an integer from 2 to 6.

In hydroxyl-containing bis(alkenyl) ethers of Formula (2), each n can be 1, 2, 3, or 4.

In hydroxyl-containing bis(alkenyl) ethers of Formula (2), $R^4$ can be $C_{2-6}$ n-alkanediyl, such as ethane-diyl, n-propane-diyl, n-butane-diyl, n-pentane-diyl, or n-hexane-diyl.

In hydroxyl-containing bis(alkenyl) ethers of Formula (2), $R^4$ can be $-[(-CH_2-)_p-X-]_q-(-CH_2-)_r-$.

In hydroxyl-containing bis(alkenyl) ethers of Formula (2), $R^4$ can be $-[(-CH_2-)_p-X-]_q-(-CH_2-)_r-$, where each X can be $-O-$, each X can be $-S-$, or each X can be $-S-S-$.

In hydroxyl-containing bis(alkenyl) ethers of Formula (2), $R^4$ can be $-[(-CH_2-)_p-X-]_q-(-CH_2-)_r-$, where each p can be 2 and r can be 2.

In hydroxyl-containing bis(alkenyl) ethers of Formula (2), $R^4$ can be $-[(-CH_2-)_p-X-]_q-(-CH_2-)_r-$, where q can be 1, 2, 3, 4, or 5.

In hydroxyl-containing bis(alkenyl) ethers of Formula (2), $R^4$ can be $-[(-CH_2-)_p-X-]_q-(-CH_2-)_r-$, where each p can be 2 and r can be 2; and q can be 1, 2, 3, 4, or 5.

In hydroxyl-containing bis(alkenyl) ethers of Formula (2), $R^4$ can be $-[(-CH_2-)_p-X-]_q-(-CH_2-)_r-$, where each X can be $-S-$; each p can be 2 and r can be 2; and q can be 1, 2, 3, 4, or 5.

In hydroxyl-containing bis(alkenyl) ethers of Formula (2), $R^4$ can be $-[(-CH_2-)_p-X-]_q-(-CH_2-)_r-$, where each X can be $-O-$; each p is 2 and r can be 2; and q can be 1, 2, 3, 4, or 5.

In hydroxyl-containing bis(alkenyl) ethers of Formula (2), $R^4$ can be $-[(-CH_2-)_p-X-]_q-(-CH_2-)_r-$, where each X can be $-S-S-$.

Examples of suitable hydroxyl-containing bis(alkenyl) ethers include 3,10,13,20-tetraoxa-7,16-dithiatricosa-1,2-diene-5,18-diol, 4,18-dioxa-8,11,14-trithiahenicosa-1,20-diene-6,16-diol, 4,11,18-trioxa-8,14-dithiahenicosa-1,20-diene-6,16-diol, and 4,15-dioxa-8,11-dithiaoctadeca-1,17-diene-6,13-diol, and combinations of any of the foregoing.

Hydroxyl-containing bis(alkenyl) ethers can have the structure of Formula (2b), Formula (2c), Formula (2d), Formula (2e), or a combination of any of the foregoing:

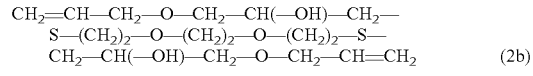     (2b)

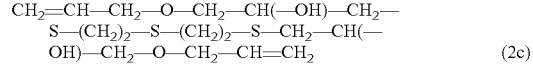     (2c)

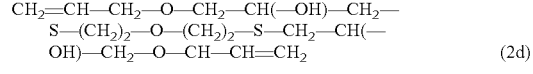     (2d)

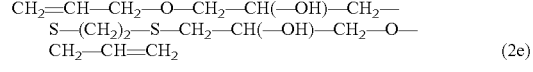     (2e)

A hydroxyl-containing bis(alkenyl) ether provided by the present disclosure can be liquid at room temperature. A hydroxyl-containing bis(alkenyl) ether can have an number average molecular weight from 200 Daltons to 2,000 Daltons, from 200 Daltons to 1,500 Daltons, from 200 Daltons to 1,000 Daltons, from 200 Daltons to 800 Daltons, or from 300 Daltons to 500 Daltons. The number average molecular weight can be determined by end group analysis using iodine titration.

Hydroxyl-containing bis(alkenyl) ethers can be prepared by reacting a dithiol with an epoxy vinyl ether in the presence of a base at elevated temperature.

Hydroxyl-containing bis(alkenyl) ethers can be prepared by reacting a dithiol with an epoxy vinyl ether.

A hydroxyl-containing bis(alkenyl) ether can comprise reaction products of reactants comprising:

(a) a dithiol of Formula (6):

$$HS-R^4-SH \quad (6)$$

wherein, $R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-X-]_q-(-CH_2-)_r-$, wherein, each X is independently selected from $-O-$, $-S-$ and $-S-S-$;

each p is independently an integer from 2 to 6;

q is an integer from 1 to 5; and r is an integer from 2 to 6; and (b) a compound having the structure of Formula (8):

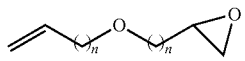
(8)

wherein each n is independently an integer from 1 to 4.

The moiety $-CH(-O-CH_2-)$ represents an epoxy group.

In compounds of Formula (6), $R^4$ can be $C_{2-6}$ n-alkanediyl, such as ethane-diyl, n-propane-diyl, n-butane-diyl, n-pentane-diyl, or n-hexane-diyl.

In compounds of Formula (6), $R^4$ can be $-[(-CH_2-)_p-X-]_q-(-CH_2-)_r-$.

In compounds of Formula (6), $R^4$ can be $-[(-CH_2-)_p-X-]_q-(-CH_2-)_r-$, where each X can be $-O-$ or each X can be $-S-S-$.

In compounds of Formula (6), $R^4$ can be $-[(-CH_2-)_p-X-]_q-(-CH_2-)_r-$, where each X can be $-S-$.

In compounds of Formula (6), $R^4$ can be $-[(-CH_2-)_p-X-]_q-(-CH_2-)_r-$, where each p can be 2 and r can be 2.

In compounds of Formula (6), $R^4$ can be $-[(-CH_2-)_p-X-]_q-(-CH_2-)_r-$, where q can be 1, 2, 3, 4, or 5.

In compounds of Formula (6), $R^4$ can be $-[(-CH_2-)_p-X-]_q-(-CH_2-)_r-$, where each p can be 2 and r can be 2; and q can be 1, 2, 3, 4, or 5.

In compounds of Formula (6), $R^4$ can be $-[(-CH_2-)_p-X-]_q-(-CH_2-)_r-$, where each X can be $-S-$; each p can be 2 and r can be 2; and q can be 1, 2, 3, 4, or 5.

In compounds of Formula (6), $R^4$ can be $-[(-CH_2-)_p-X-]_q-(-CH_2-)_r-$, where each X can be $-O-$; each p can be 2 and r can be 2; and q can be 1, 2, 3, 4, or 5.

In compounds of Formula (6), $R^4$ can be $-[(-CH_2-)_p-X-]_q-(-CH_2-)_r-$, at least one X can be $-O-$ and at least one X can be $-S-$.

A compound of Formula (6) can comprise dimercaptodioxaoctane (3,6-dioxa-1,8-octanedithiol; DMDO), dimercaptodiethylsulfide (2,2'-thiobis(ethane-1-thiol); DMDS), 2,2'-oxybis(ethane-1-thiol), 1,2-ethanedithiol, or a combination of any of the foregoing.

A compound of Formula (6) can comprise a compound of Formula (6a), Formula (6b), Formula (6c), Formula (6d), Formula (6e), or a combination of any of the foregoing:

$$HS-(CH_2)_2-O-(CH_2)_2-O-(CH_2)_2-SH \quad (6a)$$

$$HS-(CH_2)_2-S-(CH_2)_2-SH \quad (6b)$$

$$HS-(CH_2)_2-O-(CH_2)_2-SH \quad (6c)$$

$$HS-(CH_2)_2-SH \quad (6d)$$

$$HS-(CH_2)_2-O-(CH_2)_2-S-(CH_2)_2-SH \quad (6e)$$

Compounds of Formula (8) can be referred to as epoxy vinyl ethers.

In epoxy vinyl ethers of Formula (8), n can be 1, 2, 3, or 4. In epoxy vinyl ethers of Formula (8), n can be 1.

For example, an epoxy vinyl ether of Formula (8) can be 2-((allyloxy)methyl)oxirane (allyl glycidyl ether), 2-(2-(allyloxy)ethyl)oxirane, 2-(3-(allyloxy)propyl)oxirane, or a combination of any of the foregoing.

Hydroxyl-containing bis(alkenyl) ethers can be prepared by reacting a dithiol with an epoxy vinyl ether in the presence of a base at elevated temperature.

Divinyl ethers can have the structure of Formula (3):

$$CH_2=CH-O-(-R^2-O-)_m-CH=CH_2 \quad (3)$$

wherein, m is 0 to 50; and each $R^2$ independently comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-O-]_q-(-CH_2-)_r-$, wherein, each p is independently an integer ranging from 2 to 6;

q is an integer from 1 to 5; and r is an integer from 2 to 10.

In divinyl ethers of Formula (3), m can be an integer from 0 to 50, such as an integer from 1 to 6, from 1 to 4, or from 1 to 3.

In divinyl ethers of Formula (3), m can be 1, 2, 3, 4, 5, or 6.

In divinyl ethers of Formula (3), each $R^2$ can independently be $C_{2-6}$ alkanediyl such as 1,2-ethane-diyl, 1,3-propane-diyl, 1,4-butane-diyl, 1,5-pentane-diyl, or 1,6-hexane-diyl.

In divinyl ethers of Formula (3), each $R^2$ can be $-[(-CH_2-)_p-O-]_q-(-CH_2-)_r-$.

In divinyl ethers of Formula (3), each $R^2$ can be $-[(-CH_2-)_p-O-]_q-(-CH_2-)_r-$, where each p can be 2, each r can be 2, and q can be 1, 2, 3, 4, or 5.

Examples of suitable divinyl ethers include divinyl ether, ethylene glycol divinyl ether (EG-DVE), butanediol divinyl ether (BD-DVE), hexanediol divinyl ether (HD-DVE), diethylene glycol divinyl ether (DEG-DVE), triethylene glycol divinyl ether (TEG-DVE), tetraethylene glycol divinyl ether, and cyclohexanedimethanol divinyl ether.

Suitable divinyl ethers include, for example, compounds having at least one oxyalkanediyl group, such as from 1 to 4 oxyalkanediyl groups, i.e., compounds in which m in Formula (3) is an integer from 1 to 4. M in Formula (3) can be an integer ranging from 2 to 4. It is also possible to employ commercially available divinyl ether mixtures that are characterized by a non-integral average value for the number of oxyalkanediyl units per molecule. Thus, m in Formula (3) can also take on rational number values ranging from 0 to 10.0, such as from 1.0 to 10.0, from 1.0 to 4.0, or from 2.0 to 4.0.

Examples of suitable divinyl ethers include, divinyl ether, ethylene glycol divinyl ether (EG-DVE) ($R^2$ in Formula (3) is ethanediyl and m is 1), butanediol divinyl ether (BD-DVE) ($R^2$ in Formula (3) is butanediyl and m is 1), hexanediol divinyl ether (HD-DVE) ($R^2$ in Formula (3) is hexanediyl and m is 1), diethylene glycol divinyl ether (DEG-DVE) ($R^2$ in Formula (3) is ethanediyl and m is 2), triethylene glycol divinyl ether ($R^2$ in Formula (3) is ethanediyl and m is 3), tetraethylene glycol divinyl ether (TEG-DVE) ($R^2$ in Formula (3) is ethanediyl and m is 4), cyclohexanedimethanol divinyl ether, polytetrahydrofuryl divinyl ether; trivinyl ether monomers, such as trimethylolpropane trivinyl ether; tetrafunctional ether monomers, such as pentaerythritol tetravinyl ether; and combinations of two or more such divinyl ether monomers. A divinyl ether may have one or more pendant groups selected from alkyl groups, hydroxyl groups, alkoxy groups, and amino groups.

Divinyl ethers in which $R^2$ in Formula (3) is $C_{3-6}$ branched alkanediyl may be prepared by reacting a polyhydroxy compound with acetylene. Examples of divinyl ethers of this type include compounds in which $R^2$ in Formula (3) is an alkyl-substituted methanediyl group such as —CH(CH$_3$)— (for example Pluriol® blends such as Pluriol® E-200 divinyl ether (BASF Corporation), for which $R^2$ in Formula (3) is ethanediyl and m is 3.8) or an alkyl-substituted ethanediyl (for example —CH$_2$CH(CH$_3$)— such as DPE polymeric blends including DPE-2 and DPE-3, International Specialty Products).

Other useful divinyl ethers include compounds in which $R^2$ in Formula (3) is polytetrahydrofuryl (poly-THF) or polyoxyalkanediyl, such as those having an average of about 3 monomer units.

Hydroxyl-containing bis(alkenyl) ethers of Formula (2) are difunctional. Hydroxyl-containing bis(alkenyl) ethers provided by the present disclosure also include multifunctional hydroxyl-containing bis(alkenyl) ethers having a functionality greater than two, such as a functionality from 3 to 6.

For example, a hydroxyl-containing bis(alkenyl) ether can have the structure of Formula (7):

wherein,
B comprises a core of a z-valent polyfunctionalizing agent B(—V)$_z$;
z is an integer from 3 to 6; and
each —V is a moiety comprising a terminal hydroxyl-containing bis(alkenyl) ether group.

A multifunctional hydroxyl-containing bis(alkenyl) ether can be derived from a hydroxyl-containing bis(alkenyl) ether of Formula (2).

For example, a polyfunctional hydroxyl-containing bis (alkenyl) ether can have the structure of Formula (10):

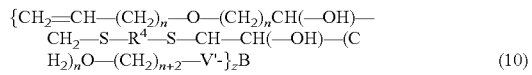

where n and $R^4$ are defined as in Formula (2), z and B are defined as in Formula (7), and V' can be derived from the reaction of V with an alkenyl group.

In multifunctional hydroxyl-containing bis(alkenyl) ethers of Formula (10), B(—V)$_z$ can be a polythiol such as any of those disclosed herein, such as 1,2,3-propane trithiol and isocyanurate-containing trithiols.

Multifunctional hydroxyl-containing bis(alkenyl) ethers of Formula (10) can be prepared by reacting a hydroxyl-containing bis(alkenyl) ether of Formula (2) with a thiol-terminated polyfunctionalizing agent B(—V)$_z$ in the presence of a suitable catalyst such as an amine catalyst.

Multifunctional hydroxyl-containing bis(alkenyl) ethers can be used to prepare hydroxyl-containing bis(alkenyl) ether-containing polythioether prepolymers provided by the present disclosure. For example, the reactants can include multifunctional hydroxyl-containing bis(alkenyl) ethers as part of the alkenyl component. Multifunctional hydroxyl-containing bis(alkenyl) ethers can be the only polyfunctional reactant having a functionality greater than 2 or may be used in combination with a thiol-terminated polyfunctionalizing agent.

For example, polythioether prepolymers provided by the present disclosure can comprise reaction products of reactants comprising:

(a) a polythiol, wherein the polythiol comprises dithiol of Formula (6), a polythiol of Formula (7), or a combination thereof:

wherein $R^1$ comprises $C_{2-10}$ alkanediyl, $C_{6-8}$ cycloalkanediyl, $C_{6-10}$ alkanecycloalkanediyl, $C_{5-8}$ heterocycloalkanediyl, or —[(—CHR—)$_p$—X—]$_q$—(—CHR—)$_r$—, wherein:
each p is independently an integer from 2 to 6;
q is an integer from 1 to 5;
r is an integer from 2 to 10;
each R is independently selected from hydrogen and methyl; and
each X is independently selected from —O—, —S—, and —NR$^5$—, wherein $R^5$ is selected from hydrogen and methyl;

wherein,
B comprises a core of a z-valent polyfunctionalizing agent B(—V)$_z$;
z is an integer from 3 to 6; and
each —V is independently a moiety comprising a terminal alkenyl group or a terminal thiol group;

(b) a hydroxyl-containing bis(alkenyl) ether, wherein the hydroxyl-containing bis(alkenyl) ether comprises a hydroxyl-containing bis(alkenyl) ether of Formula (2), a hydroxyl-containing bis(alkenyl) ether of formula (10), or a combination thereof:

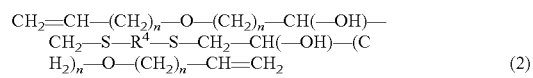

wherein,
each n is independently an integer from 1 to 4; and
$R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or —[(—CH$_2$—)$_p$—X—]$_q$—(—CH$_2$—)$_r$—, wherein,
each X is independently selected from —O—, —S— and —S—S—;
each p is independently an integer from 2 to 6;
q is an integer from 1 to 5; and
r is an integer from 2 to 6;

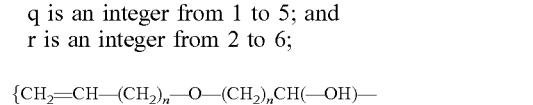

wherein,
B comprises a core of a z-valent polyfunctionalizing agent B(—V)$_z$;
z is an integer from 3 to 6; and
each —V is independently a moiety comprising a terminal alkenyl group or a terminal thiol group; and (c) a divinyl ether of Formula (3):

wherein,
m is 0 to 50; and
each $R^2$ independently comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-O-]_q-(-CH_2-)_r-$, wherein, each p is independently an integer ranging from 2 to 6; q is an integer from 1 to 5; and r is an integer from 2 to 10.

Polyfunctional hydroxyl-containing bis(alkenyl) ethers can also be terminated in a suitable functional group as appropriate for a particular curing chemistry. For example, a polyfunctional hydroxyl-containing bis(alkenyl) ether can comprise terminal thiol, epoxy, isocyanate, hydroxyl, amino, or Michael acceptor group. Polyfunctional hydroxyl-containing bis(alkenyl) ethers can have the structure of Formula (10a):

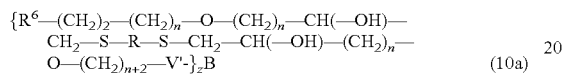
(10a)

where n and $R^4$ are defined as in Formula (2), z and B are defined as in Formula (7), V' can be derived from the reaction of V with an alkenyl group, and each $R^6$ comprises a suitable terminal functional group.

Polythioether prepolymers provided by the present disclosure are liquid at room temperature and can have a glass transition temperature Tg, for example, less than $-20°$ C., less than $-30°$ C., or less than $-40°$ C. The glass transition temperature Tg was determined by Differential Scanning Calorimetry (DSC) using a temperature ramp of 10° C./min with the Tg identified as the point at which the endotherm begins. Alternatively, Tg was determined by Dynamic Mass Analysis (DMA) using a TA Instruments Q800 apparatus with a frequency of 1 Hz, an amplitude of 20 microns, and a temperature ramp of $-80°$ C. to $25°$ C., with the Tg identified as the peak of the tan δ curve.

The polythioether prepolymers can have a viscosity from 20 poise to 500 poise, from 20 poise to 200 poise or from 40 poise to 120 poise, measured using a Brookfield CAP 2000 viscometer, using spindle #6, 25° C., at 300 rpm.

Polythioether prepolymers provided by the present disclosure can be characterized by a number average molecular weight and/or a molecular weight distribution. Polythioether prepolymers can exhibit a number average molecular weight ranging from 500 Daltons to 20,000 Daltons, from 2,000 Daltons to 5,000 Daltons, or from 1,000 Daltons to 4,000 Daltons. Polythioether prepolymers can exhibit a polydispersity (Mw/Mn; weight average molecular weight/number average molecular weight) ranging from 1 to 20, or from 1 to 5. The average number molecular weight and molecular weight distribution of polythioether prepolymers may be characterized by end group analysis using iodine titration.

Compositions provided by the present disclosure can comprise a polythioether prepolymer provided by the present disclosure such as a polythioether prepolymer of Formula (1), a thiol-terminated polythioether prepolymer of Formula (1c) and/or Formula (1d), a terminal-modified polythioether prepolymer of Formula (1a) and/or Formula (1b), or a combination of any of the foregoing.

A composition can comprise a polythioether prepolymer provided by the present disclosure as the only prepolymer or may contain additional hydroxyl-containing prepolymers. For example, in addition to a hydroxyl-containing bis(alkenyl) ether-containing polythioether prepolymer provided by the present disclosure, a composition may comprise a thiol-terminated polythioether prepolymer of Formula (11a) and/or Formula (11b), or depending on the curing chemistry, may comprise a terminal-modified polythioether prepolymer of Formula (11c) and/or Formula (11d):

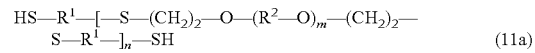
(11a)

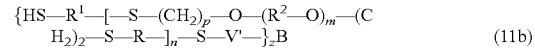
(11b)

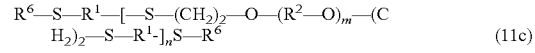
(11c)

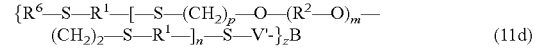
(11d)

where,
each $R^1$ comprises $C_{2-10}$ alkanediyl, $C_{6-8}$ cycloalkanediyl, $C_{6-14}$ alkanecycloalkanediyl, $C_{5-8}$ heterocycloalkanediyl, or $-[(-CHR-)_p-X-]_q-(-CHR-)_r-$, wherein:
p is an integer from 2 to 6;
q is an integer from 1 to 5;
r is an integer from 2 to 10;
each R is independently selected from hydrogen and methyl; and
each X is independently selected from $-O-$, $-S-$, and $-NR-$, wherein R is selected from hydrogen and methyl;
each $R^2$ comprises $C_{1-10}$ alkanediyl, $C_{6-8}$ cycloalkanediyl, $C_{6-14}$ alkanecycloalkanediyl, or $-[(-CHR-)_p-X-]_q-(-CHR-)_r-$, wherein p, q, r, R, and X are as defined as for $R^1$;
m is an integer from 0 to 50;
n is an integer from 1 to 60;
B represents a core of a z-valent polyfunctionalizing agent $B(-V)_z$ wherein:
z is an integer from 3 to 6; and
each V is a group comprising a terminal group reactive with a thiol group; and
each $-V'-$ is derived from the reaction of $-V$ with a thiol.

In prepolymers of Formula (11a)-(11d), $R^1$ can be $-[(-CH_2-)_p-X-]_q-(CH_2)_r-$, where p can be 2, X can be $-O-$, q can be 2, r can be 2, $R^2$ can be ethanediyl, m can be 2, and n can be 9.

In prepolymers of Formula (11a)-(11d), $R^1$ can be selected from $C_{2-6}$ alkanediyl and $-[-(CHR)_p-X-]_q-(CHR)_r-$.

In prepolymers of Formula (11a)-(11d), $R^1$ can be $-[-(CHR)_p-X-]_q-(CHR)_r-$ where X can be $-O-$ or, X can be $-S-$.

In prepolymers of Formula (11a)-(11d), $R^1$ can be $-[-(CHR)_p-X-]_q-(CHR)_r-$, p can be 2, r can be 2, q can be 1, and X can be $-S-$; or p can be 2, q can be 2, r can be 2, and X can be $-O-$; or p can be 2, r can be 2, q can be 1, and X can be $-O-$.

In prepolymers of Formula (11a)-(11d), where $R^1$ can be $-[-(CHR)_p-X-]_q-(CHR)_r-$, each $R^3$ can be hydrogen or at least one R can be methyl.

In prepolymers of Formula (11a)-(11d), each $R^1$ can be the same or at least one $R^1$ can be different.

Various methods can be used to prepare such polythioether prepolymers. Examples of suitable thiol-terminated polythioether prepolymers, and methods for their production, are described, for example, in U.S. Pat. No. 6,172,179. Such thiol-terminated polythioether prepolymers may be difunctional, that is, linear prepolymers having two thiol terminal groups, or polyfunctional, that is, branched prepolymers have three or more thiol terminal groups. Thiol-terminated polythioether prepolymers may also comprise a combination of difunctional and polyfunctional thiol-terminated polythioether prepolymers. Suitable thiol-terminated polythioether prepolymers are commercially available, for example, as Permapol® P3.1E, from PRC-DeSoto International Inc.

Suitable thiol-terminated polythioether prepolymers may be produced by reacting a divinyl ether or mixtures of divinyl ethers with an excess of dithiol or a mixtures of dithiols. For example, dithiols suitable for use in preparing thiol-terminated polythioether prepolymers include those of Formula (5), other dithiols disclosed herein, or combinations of any of the dithiols disclosed herein.

A dithiol can have the structure of Formula (6):

wherein:
R$^1$ comprises C$_{2-6}$ alkanediyl, C$_{6-8}$ cycloalkanediyl, C$_{6-10}$ alkanecycloalkanediyl, C$_{5-8}$ heterocycloalkanediyl, or —[—(CHR$^3$)$_p$—X—]$_q$—(CHR$^3$)$_r$—;
wherein:
each R$^3$ is independently selected from hydrogen and methyl;
each X is independently selected from —O—, —S—, —NH—, and —N(—CH$_3$)—;
p is an integer from 2 to 6;
q is an integer from 1 to 5; and
r is an integer from 2 to 10.

Suitable divinyl ethers for preparing thiol-terminated polythioethers prepolymers include divinyl ethers of Formula (3):

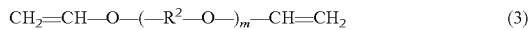

where R$^2$ in Formula (3) comprises C$_{2-6}$ n-alkanediyl group, a C$_{3-6}$ branched alkanediyl group, a C$_{6-8}$ cycloalkanediyl group, a C$_{6-10}$ alkanecycloalkanediyl group, or —[(—CH$_2$—)$_p$—O—]$_q$—(—CH$_2$—)$_r$—, where p is an integer ranging from 2 to 6, q is an integer from 1 to 5, and r is an integer from 2 to 10. In a divinyl ether of Formula (3), R$^2$ can be a C$_{2-6}$ n-alkanediyl group, a C$_{3-6}$ branched alkanediyl group, a C$_{6-8}$ cycloalkanediyl group, a C$_{6-10}$ alkanecycloalkanediyl group, or —[(—CH$_2$—)$_p$—O—]$_q$—(—CH$_2$—)$_r$—.

Two or more types of divinyl ether monomers of Formula (3) may be used. Thus, two dithiols of Formula (6) and one divinyl ether monomer of Formula (3), one dithiol of Formula (6) and two divinyl ether monomers of Formula (3), two dithiols of Formula (6) and two divinyl ether monomers of Formula (3), and more than two dithiols or divinyl ethers of one or both Formula (6) and Formula (3), may be used to produce a variety of thiol-terminated polythioether prepolymers.

A divinyl ether monomer can comprise 20 mole percent to less than 50 mole percent of the reactants used to prepare a thiol-terminated polythioether prepolymer, or 30 mole percent to less than 50 mole percent.

Relative amounts of dithiols and divinyl ethers can be selected to yield polythioether prepolymers having terminal thiol groups. Thus, a dithiol of Formula (6) or a mixture of at least two different dithiols of Formula (6), can be reacted with of a divinyl ether of Formula (3) or a mixture of at least two different divinyl ethers of Formula (3) in relative amounts such that the molar ratio of thiol groups to vinyl groups is greater than 1:1, such as from 1.1:1.0 to 2.0:1.0.

The reaction between compounds of dithiols and divinyl ethers may be catalyzed by a free radical catalyst. Suitable free radical catalysts include, for example, azo compounds, for example azobisnitriles such as azo(bis)isobutyronitrile (AIBN); organic peroxides such as benzoyl peroxide and t-butyl peroxide; and inorganic peroxides such as hydrogen peroxide. The catalyst may be, for example, a free-radical catalyst, an ionic catalyst, or ultraviolet radiation. A catalyst may not comprise an acidic or basic compound, and may not produce acidic or basic compounds upon decomposition. Examples of free-radical catalysts include azo-type catalyst, such as Vazo®-57 (Du Pont), Vazo®-64 (Du Pont), Vazo®-67 (Du Pont), V-70® (Wako Specialty Chemicals), and V-65B® (Wako Specialty Chemicals). Examples of other free-radical catalysts include alkyl peroxides, such as t-butyl peroxide. The reaction may also be effected by irradiation with ultraviolet light either with or without a cationic photoinitiating moiety.

Thiol-terminated polythioether prepolymers provided by the present disclosure may be prepared by combining at least one dithiol of Formula (6) and at least one divinyl ether of Formula (3) followed by addition of an appropriate catalyst, and carrying out the reaction at a temperature from 30° C. to 120° C., such as 70° C. to 90° C., for a time from 2 hours to 24 hours, such as from 2 hours to 6 hours.

Thiol-terminated polythioether prepolymers may comprise a polyfunctional polythioether prepolymer having an average functionality of greater than 2.0. Suitable polyfunctional thiol-terminated polythioether prepolymers include, for example, those having the structure of Formula (12):

wherein: (i) -A- comprises, for example, a structure of Formula (1), (ii) B denotes a z-valent residue of a polyfunctionalizing agent; and (iii) z has an average value of greater than 2.0, and, a value between 2 and 3, a value between 2 and 4, a value between 3 and 6, or can be an integer from 3 to 6.

Sulfur-containing polyformal prepolymers useful in aerospace sealant applications are disclosed, for example, in U.S. Application Publication No. 2012/0234205 and in U.S. Application Publication No. 2012/0238707, each of which is incorporated by reference in its entirety.

The backbone of these polythioether prepolymers can be modified to improve the properties such as adhesion, tensile strength, elongation, UV resistance, hardness, and/or flexibility of sealants and coatings prepared using polythioether prepolymers. For example, adhesion promoting groups, antioxidants, metal ligands, and/or urethane linkages can be incorporated into the backbone of a polythioether prepolymer to improve one or more performance attributes. Examples of backbone-modified polythioethers are disclosed, for example, in U.S. Pat. No. 8,138,273 (urethane containing), U.S. Application Publication No. 2015/0240122 (sulfone-containing), U.S. Pat. No. 8,952,124 (bis(sulfonyl)alkanol-containing), U.S. Application Publication No. 2015/0240140 (metal-ligand containing), U.S. application Ser. No. 14/922,280 (antioxidant containing), each of which is incorporated by reference in its entirety.

A composition may comprise a sulfur-containing prepolymer such as a polythioether prepolymer, a polysulfide prepolymer, a sulfur-containing polyformal prepolymer, or a combination of any of the foregoing.

A sulfur-containing polymer can comprise a polythioether, a polysulfide, a sulfur-containing polyformal, or a combination of any of the foregoing. A sulfur-containing prepolymer can comprise a polythioether or a sulfur-containing polymer can comprise a polysulfide. A sulfur-containing polymer may comprise a mixture of different polythioethers and/or polysulfides, and the polythioethers and/or polysulfides may have the same or different functionality. A sulfur-containing polymer can have an average functionality from 2 to 6, from 2 to 4, from 2 to 3, from 2.3 to 2.8, or from 2.05 to 2.5. For example, a sulfur-containing prepolymer can be selected from a difunctional sulfur-containing prepolymer, a trifunctional sulfur-containing prepolymer, and a combination thereof. A sulfur-containing prepolymer can comprise a sulfur-containing polyformal.

A sulfur-containing prepolymer can be thiol-terminated. Examples of thiol-terminated polythioethers are disclosed, for example, in U.S. Pat. No. 6,172,179. A thiol-terminated polythioether can comprise Permapol® P3.1E, and Permapol® L56086, or a combination of any of the foregoing, each of which is available from PRC-DeSoto International Inc.

Examples of suitable polysulfides are disclosed, for example, in U.S. Pat. Nos. 4,623,711; 6,172,179; 6,509,418; 7,009,032; and 7,879,955, each of which is incorporated by reference in its entirety.

As used herein, the term polysulfide refers to a prepolymer that contains one or more polysulfide linkages, i.e., —$S_x$— linkages, where x is from 2 to 4, in the prepolymer backbone and/or in pendant positions on the prepolymer chain. A polysulfide prepolymer can have two or more sulfur-sulfur linkages. Suitable polysulfides are commercially available, for example, from AkzoNobel and Toray Fine Chemicals under the names Thiokol-LP® and Thioplast®. Thioplast® products are available in a wide range of molecular weights ranging, for example, from less than 1,100 Daltons to over 8,000 Daltons, with molecular weight being the average molecular weight in grams per mole. In some cases, the polysulfide has a number average molecular weight of 1,000 Daltons to 4,000 Daltons. The crosslink density of these products also varies, depending on the amount of crosslinking agent used. The —SH content, i.e., thiol or mercaptan content, of these products can also vary. The mercaptan content and molecular weight of the polysulfide can affect the cure speed of the prepolymer, with cure speed increasing with molecular weight.

A sulfur-containing prepolymer curing agent can comprise a polysulfide selected from a Thiokol-LP® polysulfide, a Thioplast® polysulfide, and a combination thereof, such as Thioplast® G131, Thioplast® G21 and a combination thereof.

Compositions provided by the present disclosure can comprise a suitable curing agent. A curing agent can be selected to react with the terminal group of a polythioether prepolymer provided by the present disclosure.

For example, for a thiol-terminated prepolymer provided by the present disclosure, a suitable curing agent can be a polyalkenyl compound, a polyepoxide, a polyol, a polyisocyanate, a polyamine, or a polyfunctional Michael addition donor.

Examples of useful curing agents that are reactive with alkenyl groups include dithiols and polythiols, examples of which are disclosed herein.

Hydroxyl-containing bis(alkenyl) ethers provided by the present disclosure may also be used as curing agents. For example, a polyalkenyl curing agent may comprise a hydroxyl-containing bis(alkenyl) ether of Formula (2). A polyalkenyl curing agent may comprise a hydroxyl-containing bis(alkenyl) ether provided by the present disclosure and one or more additional polyalkenyl curing agents such as any of those disclosed herein.

Examples of useful curing agents that are reactive with isocyanate groups include diamines, polyamines, polythiols, and polyols, including those disclosed herein.

Examples of useful curing agents that are reactive with hydroxyl groups include diisocyanates and polyisocyanates, examples of which are disclosed herein.

Compositions provided by the present disclosure may contain from about 90% to about 150% of the stoichiometric amount, from about 95% to about 125%, or from about 95% to about 105% of the amount of the selected curing agent(s).

Thiol-terminated hydroxyl-containing bis(alkenyl) ethers provided by the present disclosure such as the thiol-terminated hydroxyl-containing bis(alkenyl) ethers of Formula (13), and Formula (14) may also be used with polyalkenyl reactants.

Curing agents can be monomeric low molecular weight compounds or can be polymeric.

A composition can include an approximately equal equivalent number of thiol groups to functional groups of the curing agent.

Compositions provided by the present disclosure can be formulated a sealants or coatings, such as sealants or coatings suitable for use in the aerospace industry. For example, a composition formulated as a sealant may comprises fillers, antioxidants, pigments, reactive diluents, adhesion promoters, catalysts, solvents, and combinations of any of the foregoing.

Compositions provided by the present disclosure can include a filler. A filler can be included to improve the physical properties of a cured composition, to reduce the weight of a cured composition, to impart electrical conductivity to a cured composition, or to impart RFI/EMI shielding effectiveness to a cured composition.

Compositions provided by the present disclosure may comprise one or more catalysts. A suitable catalyst can be selected depending on the particular curing chemistry employed by the composition.

For example, for a thermally activated thiol-ene curing chemistry, a suitable catalyst can comprise a primary or secondary amine. For a UV activated thiol-ene curing chemistry, a suitable catalyst can comprise a photoinitiator.

For an thiol-epoxy curing chemistry, a suitable catalyst can comprise an amine.

For a Michael addition curing chemistry, a suitable catalyst can be an amine catalyst. Examples of suitable amine catalysts for a Michael addition reaction include triethylenediamine (1,4-diazabicyclo[2.2.2]octane, DABCO), dimethylcyclohexylamine (DMCHA), dimethylethanolamine (DMEA), bis-(2-dimethylaminoethyl)ether, N-ethylmorpholine, triethylamine, 1,8-diazabicyclo[5.4.0]undecene-7 (DBU), pentamethyldiethylenetriamine (PMDETA), benzyldimethylamine (BDMA), N,N,N'-trimethyl-N'-hydroxyethyl-bis(aminoethyl)ether, and N'-(3-(dimethylamino)propyl)-N,N-dimethyl-1,3-propanediamine.

For an isocyanate-hydroxyl curing chemistry, a suitable catalyst can comprise an organotin compound.

Compositions provided by the present disclosure can comprise a hydroxyl-containing bis(alkenyl) ether provided by the present disclosure such as a bifunctional hydroxyl-containing bis(alkenyl) ether of Formula (2), a polyfunctional hydroxyl-containing bis(alkenyl) of Formula (12) or a combination thereof. A hydroxyl-containing bis(alkenyl) ether may be used, for example, as a curing agent in a composition comprising a thiol-terminated sulfur-containing prepolymer such as a thiol-terminated polythioether, a thiol-terminated polysulfide, a thiol-terminated polyformal, or a combination of any of the foregoing. A hydroxyl-containing bis(alkenyl) ether may be used, for example, as a curing agent in a composition comprising a thiol-terminated sulfur-containing prepolymer a thiol-terminated polythioether prepolymer of Formula (1c) a thiol-terminated polythioether prepolymer of (1d), or a combination thereof. In such systems, a hydroxyl-containing bis(alkenyl) ether may be used in combination with other polyalkenyl curing agents.

Compositions provided by the present disclosure may be formulated as sealants. By formulated is meant that in addition to the reactive species forming the cured polymer network, additional material can be added to a composition to impart desired properties to the uncured sealant and/or to the cured sealant. For the uncured sealant these properties can include viscosity, pH, and/or rheology. For cured sealants, these properties can include weight, adhesion, corrosion resistance, color, glass transition temperature, electrical conductivity, cohesion, and/or physical properties such as tensile strength, elongation, and hardness. Compositions provided by the present disclosure may comprise one or more additional components suitable for use in aerospace sealants and depend at least in part on the desired performance characteristics of the cured sealant under conditions of use.

Compositions provided by the present disclosure can comprise one or more adhesion promoters. The composition may contain from 0.1 wt % to 15 wt % of an adhesion promoter, less than 5 wt %, less than 2 wt %, or less than 1 wt % of an adhesion promoter, based on the total dry weight of the composition. Examples of adhesion promoters include phenolics, such as Methylon® phenolic resin, and organosilanes, such as epoxy-, mercapto- or amino-functional silanes, including, for example, Silquest® A-187 and Silquest® A-1100. Other useful adhesion promoters are known in the art.

Suitable adhesion promoters include sulfur-containing adhesion promoters such as those disclosed in U.S. Pat. Nos. 8,513,339; 8,952,124; and 9,056,949; and U.S. Application Publication No. 2014/0051789, each of which is incorporated by reference.

Compositions provided by the present disclosure may comprise one or more different types of filler. Suitable fillers include those commonly known in the art, including inorganic fillers, such as carbon black and calcium carbonate ($CaCO_3$), silica, polymer powders, and lightweight fillers. Examples of electrically non-conductive fillers include materials such as, but not limited to, calcium carbonate, mica, polyamide, fumed silica, molecular sieve powder, microspheres, titanium dioxide, chalks, alkaline blacks, cellulose, zinc sulfide, heavy spar, alkaline earth oxides, and alkaline earth hydroxides. A composition can include 5 wt % to 60 wt % of a filler or combination of fillers, 10 wt % to 50 wt %, or from 20 wt % to 40 wt %, based on the total dry weight of the composition. Compositions provided by the present disclosure may further include one or more colorants, thixotropic agents, accelerators, fire retardants, adhesion promoters, solvents, masking agents, or a combination of any of the foregoing. As can be appreciated, fillers and additives employed in a composition may be selected so as to be compatible with each other as well as the polymeric component, curing agent, and or catalyst.

Compositions provided by the present disclosure can include low density filler particles. Low density particles refers to particles that have a specific gravity of no more than 0.7, no more than 0.25, or no more than 0.1. Suitable lightweight filler particles often fall within two categories—microspheres and amorphous particles. The specific gravity of microspheres may range from 0.1 to 0.7 and include, for example, polystyrene foam, microspheres of polyacrylates and polyolefins, and silica microspheres having particle sizes ranging from 5 microns to 100 microns and a specific gravity of 0.25 (Eccospheres®). Other examples include alumina/silica microspheres having particle sizes in the range of 5 to 300 microns and a specific gravity of 0.7 (Fillite®), aluminum silicate microspheres having a specific gravity of from about 0.45 to about 0.7 (Z-Light®), calcium carbonate-coated polyvinylidene copolymer microspheres having a specific gravity of 0.13 (Dualite® 6001AE), and calcium carbonate coated acrylonitrile copolymer microspheres such as Dualite® E135, having an average particle size of about 40 m and a density of 0.135 g/cc (Henkel). Suitable fillers for decreasing the specific gravity of the composition include, for example, hollow microspheres such as Expancel® microspheres (available from AkzoNobel) or Dualite® low density polymer microspheres (available from Henkel). Compositions provided by the present disclosure can include lightweight filler particles comprising an exterior surface coated with a thin coating, such as those described in U.S. Application Publication No. 2010/0041839, which is incorporated by reference in its entirety. Suitable lightweight fillers are also disclosed in U.S. Pat. No. 6,525,168. A light weight filler can comprise polyphenylene sulfide such as disclosed in U.S. application Ser. No. 14/640,044, filed on Jan. 9, 2015, which is incorporated by reference in its entirety.

A composition can comprise less than 2 wt % of lightweight particles, less than 1.5 wt %, less than 1.0 wt %, less than 0.8 wt %, less than 0.75 wt %, less than 0.7 wt %, or less than 0.5 wt % of a composition, where wt % is based on the total dry solids weight of the composition.

A composition provided by the present disclosure can comprise light weight fillers that reduce the specific gravity of the composition. For example, a composition can have a specific gravity from 0.8 to 1, 0.7 to 0.9, from 0.75 to 0.85, from 0.9 to 1.2, from 1.0 to 1.2, or about 0.8 or about 1.1. A composition can have a specific gravity from 1.02 to 1.22, from 1.04 to 1.20, from 1.06 to 1.18, from 1.08 to 1.16, from 1.10 to 1.14, or from 1.11 to 1.13. The specific gravity of a composition can be less than about 1.2, less than about 1.1, less than about 1.0, less than 0.9, less than about 0.8, less than about 0.75, less than about 0.7, less than about 0.65, less than about 0.6, or less than about 0.55. Specific gravity refers to the ratio of the density of a substance to the density of water at room temperature and pressure. Density can be measured according to ASTM D 792 Method A.

A composition provided by the present disclosure can comprise an electrically conductive filler. Electrical conductivity and EMI/RFI shielding effectiveness can be imparted to a composition by incorporating conductive materials. The conductive elements can include, for example, metal or metal-plated particles, fabrics, meshes, fibers, and combinations thereof. The metal can be in the form of, for example, filaments, particles, flakes, or spheres. Examples of suitable metals include copper, nickel, silver, aluminum, tin, and steel. Other conductive materials that can be used to impart EMI/RFI shielding effectiveness to polymer compositions include conductive particles or fibers comprising carbon or graphite. Conductive polymers such as polythiophenes, polypyrroles, polyaniline, poly(p-phenylene) vinylene, polyphenylene sulfide, polyphenylene, and polyacetylene can also be used.

Electrically conductive fillers also include high band gap materials such as zinc sulfide and inorganic barium compounds.

Fillers used to impart electrical conductivity and EMI/RFI shielding effectiveness to polymer compositions are well known in the art. Examples of electrically conductive fillers further include electrically conductive noble metal-based fillers such as pure silver; noble metal-plated noble metals such as silver-plated gold; noble metal-plated non-noble metals such as silver plated cooper, nickel or aluminum, for example, silver-plated aluminum core particles or platinum-plated copper particles; noble-metal plated glass, plastic or ceramics such as silver-plated glass microspheres, noble-metal plated aluminum or noble-metal plated plastic microspheres; noble-metal plated mica; and other such noble-metal conductive fillers. Non-noble metal-based materials can also be used and include, for example, non-noble metal-plated non-noble metals such as copper-coated iron particles or nickel plated copper; non-noble metals, e.g., copper, aluminum, nickel, cobalt; non-noble-metal-plated-non-metals, e.g., nickel-plated graphite and non-metal materials such as carbon black and graphite. Combinations of electrically conductive fillers can also be used to meet the desired conductivity, EMI/RFI shielding effectiveness, hardness, and other properties suitable for a particular application.

The shape and size of the electrically conductive fillers used in compositions of the present disclosure can be any appropriate shape and size to impart EMI/RFI shielding effectiveness to the cured composition. For example, fillers can be of any shape that is generally used in the manufacture of electrically conductive fillers, including spherical, flake, platelet, particle, powder, irregular, fiber, and the like. In certain sealant compositions of the disclosure, a base composition can comprise Ni-coated graphite as a particle, powder or flake. The amount of Ni-coated graphite in a base composition can range from 40 wt % to 80 wt %, or can range from 50 wt % to 70 wt %, based on the total weight of the base composition. An electrically conductive filler can comprise Ni fiber. Ni fiber can have a diameter ranging from 10 µm to 50 µm and have a length ranging from 250 µm to 750 µm. A base composition can comprise, for example, an amount of Ni fiber ranging from 2 wt % to 10 wt %, or from 4 wt % to 8 wt %, based on the total weight of the base composition.

Carbon fibers, particularly graphitized carbon fibers, can also be used to impart electrical conductivity to sealant compositions. Carbon fibers formed by vapor phase pyrolysis methods and graphitized by heat treatment and which are hollow or solid with a fiber diameter ranging from 0.1 micron to several microns, have high electrical conductivity. As disclosed in U.S. Pat. No. 6,184,280, carbon microfibers, nanotubes or carbon fibrils having an outer diameter of less than 0.1 µm to tens of nanometers can be used as electrically conductive fillers. An example of graphitized carbon fiber suitable for conductive compositions of the present disclosure include Panex® 3OMF (Zoltek Companies, Inc., St. Louis, Mo.), a 0.921 µm diameter round fiber having an electrical resistivity of 0.00055 Ω-cm.

The average particle size of an electrically conductive filler can be within a range useful for imparting electrical conductivity to a polymer-based composition. For example, the particle size of the one or more fillers can range from 0.25 µm to 250 m, from 0.25 µm to 75 µm, or from 0.25 µm to 60 m. Compositions of the present disclosure can comprise Ketjenblack® EC-600 JD (AkzoNobel, Inc., Chicago, Ill.), an electrically conductive carbon black characterized by an iodine absorption of 1000 mg/g to 11500 mg/g (J0/84-5 test method), and a pore volume of 480 $cm^3$/100 g to 510 $cm^3$/100 g (DBP absorption, KTM 81-3504). An electrically conductive carbon black filler can comprise Black Pearls® 2000 (Cabot Corporation).

Electrically conductive polymers can be used to impart or modify the electrical conductivity of sealant compositions of the present disclosure. Polymers having sulfur atoms incorporated into aromatic groups or adjacent double bonds, such as in polyphenylene sulfide, and polythiophene, are known to be electrically conductive. Other electrically conductive polymers include, for example, polypyrroles, polyaniline, poly(p-phenylene) vinylene, and polyacetylene. Furthermore, thiol-terminated prepolymers can comprise aromatic sulfur groups and sulfur atoms adjacent conjugated double bonds such as vinylcyclohexene-dimercaptodioxaoctane groups incorporated into the backbone of the thiol-terminated prepolymer, to enhance the electrical conductivity.

Compositions of the present disclosure can comprise more than one electrically conductive filler and the more than one electrically conductive filler can be of the same or different materials and/or shapes. For example, a sealant composition can comprise electrically conductive Ni fibers, and electrically conductive Ni-coated graphite in the form of powder, particles and/or flakes. The amount and type of electrically conductive filler can be selected to produce a sealant composition which, when cured, exhibits a sheet resistance (four-point resistance) of less than 0.50 Ω/$cm^2$, or a sheet resistance less than 0.15 S/$cm^2$. The amount and type of filler can also be selected to provide effective EMI/RFI shielding over a frequency range from 1 MHz to 18 GHz.

Galvanic corrosion of dissimilar metal surfaces and the conductive compositions of the present disclosure can be minimized or prevented by adding corrosion inhibitors to the composition, and/or by selecting appropriate conductive fillers. The non-chromate corrosion inhibitors provided by the present disclosure can increase the corrosion resistance of sealants comprising an electrically conductive filler U.S. Pat. Nos. 5,284,888 and 5,270,364 disclose the use of aromatic triazoles to inhibit corrosion of aluminum and steel surfaces that can also be included in a sealant composition provided by the present disclosure. A sacrificial oxygen scavenger such as Zn can be used as a corrosion inhibitor. A corrosion inhibitor can comprise less than 10% by weight of the total weight of the electrically conductive composition. A corrosion inhibitor can comprise an amount ranging from 2 wt % to 8 wt % of the total weight of the electrically conductive composition. Corrosion between dissimilar metal surfaces can also be minimized or prevented by the selection of the type, amount, and properties of the conductive fillers comprising the composition.

An electrically conductive filler can be added to the base component or the accelerator component of a two-part sealant composition. An electrically conductive base composition can comprise an amount of electrically nonconductive filler from 2 wt % to 10 wt % based on the total weight of the base composition, or can range from 3 wt % to 7 wt %. An accelerator composition can comprise an amount of electrically non-conductive filler from less than 6 wt % or from 0.5% to 4% by weight, based on the total weight of the accelerator composition.

A sealant composition can comprise from about 50 wt % to about 90 wt % of a thiol-terminated polythioether prepolymer, from about 60 wt % to about 90 wt %, from about 70 wt % to about 90 wt %, or from about 80 wt % to about 90 wt % of a thiol-terminated polythioether prepolymer, where wt % is based on the total dry solids weight of the sealant composition.

A sealant composition may also include additives such as plasticizers, pigments, surfactants, adhesion promoters, thixotropic agents, fire retardants, masking agents, accelerators (such as amines, including 1,4-diaza-bicyclo[2.2.2]octane, DABCO®), and combinations of any of the foregoing. When used, the additives may be present in a composition in an amount ranging, for example, from about 0 wt % to about 60 wt %. Additives may be present in a composition in an amount ranging from about 25 wt % to 60 wt %.

Uncured sealants provided by the present disclosure can be provided as a two part system comprising a base component and an accelerator component which can be prepared and stored separately, combined, and mixed at the time of use.

The base component or composition can comprise the thiol-terminated polythioether prepolymer, a catalyst and a first portion of the non-chromate corrosion inhibitor. The accelerator component or composition can comprise the polyepoxide curing agent and a second portion of the non-chromate corrosion inhibitor. The first and second portions can comprise different components of the non-chromate corrosion inhibitor.

The base component and the accelerator component can be formulated to be rendered compatible when combined such that the constituents of the base and accelerator components can intermix and be homogeneously dispersed to provide a sealant composition for application to a substrate. Factors affecting the compatibility of the base and accelerator components include, for example, viscosity, pH, density, and temperature.

Curable compositions provided by the present disclosure can be advantageously used as sealants, and in particular, as sealants where low temperature flexibility and resistance to fuel are desirable attributes. For example, curable compositions can be used as aviation and aerospace sealants. A sealant refers to a curable composition that has the ability when cured to resist atmospheric conditions such as moisture and temperature and at least partially block the transmission of materials such as water, water vapor, fuel, solvents, and/or liquids and gases.

Uncured sealant compositions provided by the present disclosure can be formulated as suitable for a particular aerospace sealant application. For example, sealant compositions can be formulated as Class A, Class s B, or as Class C fuel resistant aerospace sealants.

A Class A sealant can be formulated for use at service temperatures from −65° F. (−54° C.) to 250° F. (121° C.) with intermittent excursions to 275° F. (135° F.). A Class A sealant is intended to be applied by brushing and can be used, for example, for as brush sealing fasteners in fuel tanks and other aircraft fuselage sealing applications. A Class A sealant can have an initial viscosity from 1 poise to 500 poise.

A Class B sealant can be formulated for use at service temperatures from −65° F. to 250° F. (−54° C. to 121° C.) and is intended for fillet sealing and other aircraft fuselage sealing applications. A Class B sealant can have an initial viscosity from 4,500 poise to 20,000 poise. A Class B sealant can be applied by extrusion, injection gun, or spatula.

A Class C sealant can be formulated for use at service temperatures from −65° F. to 250° F. (−54° C. to 121° C.) and is intended for brush and fay sealing of fuel tanks and other aircraft fuselage sealing applications. A Class C sealant can have an initial viscosity from 500 poise to 4,500 poise. A Class C sealant can be applied by brush, roller, spatula, or extrusion.

Compositions provided by the present disclosure may also comprise hydroxyl-containing bis(alkenyl) ethers and/or hydroxyl-containing bis(alkenyl) ether-containing prepolymers provided by the present disclosure. The hydroxyl-containing bis(alkenyl) ethers may function as curing agents or as co-reactants. A hydroxyl-containing bis(alkenyl) ether curing agent or co-reactant can comprise a difunctional hydroxyl-containing bis(alkenyl) ether provided by the present disclosure, a multifunctional hydroxyl-containing bis(alkenyl) ether provided by the present disclosure, or a combination thereof.

For example, in thiol-ene reactions, some or all of the alkenyl component can comprise a hydroxyl-containing bis(alkenyl) ether provided the present disclosure.

A hydroxyl-containing bis(alkenyl) ether provided by the present disclosure may be reacted with a stoichiometric excess of a dithiol or other suitable compound having a terminal functional group and a group reactive with an alkenyl group to provide a terminal-modified hydroxyl-containing bis(alkenyl) ether.

For example, a hydroxyl-containing bis(alkenyl) ether of Formula (2) can be reacted with a dithiol of Formula (6) to provide a thiol-terminated hydroxyl-containing bis(alkenyl) ether of Formula (10b):

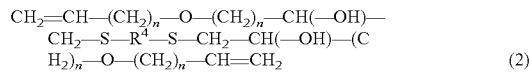

(2)

(6)

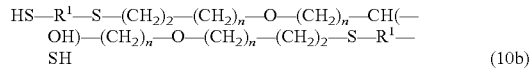

(10b)

The terminal-modified bis(alkenyl) ether may be added to a composition comprising a terminal-modified polythioether prepolymer, where the terminal-modified bis(alkenyl) ether and the terminal-modified polythioether prepolymer have the same terminal functional groups.

Compositions comprising the polythioether prepolymers provided by the present disclosure can be used as coatings and sealants useful in aerospace applications.

Compositions provided by the present disclosure may be used, for example, in sealants, coatings, encapsulants, and potting compositions. A sealant includes a composition capable of producing a film that has the ability to resist operational conditions, such as moisture and temperature, and at least partially block the transmission of materials, such as water, fuel, and other liquid and gases. A coating composition includes a covering that is applied to the surface of a substrate to, for example, improve the properties of the substrate such as the appearance, adhesion, wettability, corrosion resistance, wear resistance, fuel resistance, and/or abrasion resistance. A potting composition includes a material useful in an electronic assembly to provide resistance to shock and vibration and to exclude moisture and corrosive agents. In particular, sealant compositions provided by the present disclosure are useful as aerospace sealants and can be used, for example, in linings for fuel tanks.

Compositions, such as sealants, may be provided as multi-part compositions, such as two-part compositions, where one part comprises one or more thiol-terminated polythioether prepolymers and a second part comprises one or more polyepoxides. Additives and/or other materials may be added to either part as desired or necessary. The two parts may be combined and mixed prior to use. The working time of the mixed sealant composition can be at least 12 hours, at least 24 hours, at least 48 hours, or more than 48 hours, where working time refers to the period of time the mixed composition remains malleable, e.g., has a sufficiently low viscosity, for application to a surface after mixing.

A composition cures to a tack-free cure within about 24 hours to about 72 hours at a temperature of about 25° C. or higher after the composition is no longer workable. The time to form a viable seal using moisture-curable compositions provide by the present disclosure can depend on several factors as can be appreciated by those skilled in the art, and as defined by the requirements of applicable standards and specification. In general, curable compositions provided by the present disclosure can develop adhesion strength within about 3 days to about 7 days following application to a surface. In general, full adhesion strength as well as other properties of cured compositions provided by the present disclosure can become fully developed within 7 days following mixing and application of a curable composition to a surface.

Compositions provided by the present disclosure can have a working time greater than about 12 hours, and can cure to a Shore A hardness of 25 A in from about 150 hours to about 250 hours.

Compositions, including sealants, provided by the present disclosure may be applied to any of a variety of substrates. Examples of substrates to which a composition may be applied include metals such as titanium, stainless steel, steel alloy, aluminum, and aluminum alloy, any of which may be anodized, primed, organic-coated or chromate-coated; epoxy; urethane; graphite; fiberglass composite; Kevlar®; acrylics; and polycarbonates. Compositions provided by the present disclosure may be applied to a substrate such as aluminum and aluminum alloy.

Sealant compositions provided by the present disclosure may be formulated as Class A, Class B, or Class C sealants. A Class A sealant refers to a brushable sealant having a viscosity of 1 poise to 500 poise and is designed for brush application. A Class B sealant refers to an extrudable sealant having a viscosity from 4,500 poise to 20,000 poise and is designed for application by extrusion via a pneumatic gun. A Class B sealant can be sued to form fillets and sealing on vertical surfaces or edges where low slump/slag is required. A Class C sealant has a viscosity from 500 poise to 4,500 poise and is designed for application by a roller or combed tooth spreader. A Class C sealant can be used for fay surface sealing. Viscosity can be measured according to Section 5.3 of SAE Aerospace Standard AS5127/1C published by SAE International Group.

Compositions provided by the present disclosure may be applied directly onto the surface of a substrate or over an underlayer by any suitable coating process known to those of ordinary skill in the art.

Furthermore, methods are provided for sealing an aperture utilizing a composition provided by the present disclosure. These methods comprise, for example, providing the curable composition of the present disclosure; applying the curable composition to at least one surface of a part; and curing the applied composition to provide a sealed part.

A composition provided by the present disclosure may be cured under ambient conditions, where ambient conditions refers to a temperature from 20° C. to 25° C., and atmospheric humidity. A composition may be cured under conditions encompassing a temperature from a 0° C. to 100° C. and humidity from 0% relative humidity to 100% relative humidity. A composition may be cured at a higher temperature such as at least 30° C., at least 40° C., or at least 50° C. A composition may be cured at room temperature, e.g., 25° C. A composition may be cured upon exposure to actinic radiation, such as ultraviolet radiation. As will also be appreciated, the methods may be used to seal apertures on aerospace vehicles including aircraft and aerospace vehicles.

The time to form a viable seal using curable compositions of the present disclosure can depend on several factors as can be appreciated by those skilled in the art, and as defined by the requirements of applicable standards and specifications. In general, curable compositions of the present disclosure develop adhesion strength within about 3 days to about 7 days following mixing and application to a surface. In general, full adhesion strength as well as other properties of cured compositions of the present disclosure becomes fully developed within 7 days following mixing and application of a curable composition to a surface.

Compositions containing a hydroxyl-containing bis(alkenyl) ether-containing prepolymer provided by the present disclosure and an polyepoxide curing agent can cure, for example, in from 0.5 hours to 3 hours, from 1 hour to 2.5 hours, or from 1 hour to 2 hours, where time to cure refers the time after mixing the prepolymer and curing agent to the time at which the composition exhibits a Shore A hardness of 30. The curing time to exhibit a Shore A hardness of 40 can range, for example, from 1 hour to 4 hours, from 1.5 hour to 3.5 hour, or from 2 hours to 3 hours. Shore A hardness can be measured using Type A durometer in accordance with ASTM D2240.

Cured compositions provided by the present disclosure, such as cured sealants, exhibit properties acceptable for use in aerospace sealant applications. In general, it is desirable that sealants used in aviation and aerospace applications exhibit the following properties: peel strength greater than 20 pounds per linear inch (pli) on Aerospace Material Specification (AMS) 3265B substrates determined under dry conditions, following immersion in JRF Type I for 7 days, and following immersion in a solution of 3% NaCl according to AMS 3265B test specifications; tensile strength between 300 pounds per square inch (psi) and 400 psi; tear strength greater than 50 pounds per linear inch (pli); elongation between 250% and 300%; and hardness greater than 40 Durometer A. These and other cured sealant properties appropriate for aviation and aerospace applications are disclosed in AMS 3265B, the entirety of which is incorporated by reference. It is also desirable that, when cured, compositions of the present disclosure used in aviation and aircraft applications exhibit a percent volume swell not greater than 25% following immersion for one week at 60° C. (140° F.) and ambient pressure in Jet Reference Fluid (JRF) Type 1. Other properties, ranges, and/or thresholds may be appropriate for other sealant applications.

Cured compositions provided by the present disclosure can be fuel-resistant. The term "fuel resistant" means that a composition, when applied to a substrate and cured, can provide a cured product, such as a sealant, that exhibits a percent volume swell of not greater than 40%, in some cases not greater than 25%, in some cases not greater than 20%, and in other cases not more than 10%, after immersion for one week at 140° F. (60° C.) and ambient pressure in JRF Type I according to methods similar to those described in ASTM D792 (American Society for Testing and Materials) or AMS 3269 (Aerospace Material Specification). JRF Type I, as employed for determination of fuel resistance, has the following composition: toluene: 28±1% by volume; cyclohexane (technical): 34±1% by volume; isooctane: 38±1% by volume; and tertiary dibutyl disulfide: 1±0.005% by volume (see AMS 2629, issued Jul. 1, 1989, § 3.1.1 etc., available from SAE (Society of Automotive Engineers)).

Compositions provided by the present disclosure provide a cured product, such as a sealant, exhibiting a tensile elongation of at least 200% and a tensile strength of at least 200 psi when measured in accordance with the procedure described in AMS 3279, § 3.3.17.1, test procedure AS5127/1, § 7.7. In general, for a Class A sealant there is no tensile and elongation requirement. For a Class B sealant, as a general requirement, tensile strength is equal to or greater than 200 psi and elongation is equal to or greater than 200%. Acceptable elongation and tensile strength can be different depending on the application.

Compositions provide a cured product, such as a sealant, that exhibits a lap shear strength of greater than 200 psi, such as at least 220 psi, at least 250 psi, and, in some cases, at least 400 psi, when measured according to the procedure described in SAE AS5127/1 paragraph 7.8.

A cured sealant prepared from a composition provided by the present disclosure meets or exceeds the requirements for aerospace sealants as set forth in AMS 3277.

Apertures, surfaces, joints, fillets, fay surfaces including apertures, surfaces, fillets, joints, and fay surfaces of aerospace vehicles, sealed with compositions provided by the present disclosure are also disclosed.

An electrically conductive sealant composition provided by the present disclosure can exhibit the following properties measured at room temperature following exposure at 500° F. for 24 hours: a surface resistivity of less than 1 ohms/square, a tensile strength greater than 200 psi, an elongation greater than 100%, and a cohesive failure of 100% measured according to MIL-C-27725.

Cured compositions comprising hydroxyl-containing bis (alkenyl)ether-containing polythioether prepolymers can exhibit improved tensile strength compared to cured compositions comprising polythioether prepolymers prepared using divinyl ethers without pendent hydroxyl groups. The enhanced tensile strength is believed to be the result of hydrogen bonding of the hydroxyl groups within the polymer network.

Compositions comprising hydroxyl-containing bis(alkenyl)ether-containing polythioether prepolymers can exhibit reduced viscosity. Low viscosity is particularly important for compositions comprising fillers. It is desirable to add fillers to a polymeric composition, for example, to impart electrical conductivity, or to reduce the weight of a sealant or coating using light weight (low specific gravity) fillers. For example, the viscosity of a composition comprising a polymeric light weight filler, such as Expancel®. High viscosity renders a composition difficult to apply. To maintain workability of a composition, the upper limit of light weight filler that can be included in the composition can be 1 wt %, where wt % is based on the total weight of the composition. Using the inventive hydroxyl-containing bis(alkenyl)ether-containing polythioether prepolymers, a content of light weight filler such as silica up to 3 wt % can be used and still maintain a sufficiently low viscosity that the composition remains workable for at least a few hours.

Hydroxyl-containing bis(alkenyl)ether-containing polythioether prepolymers and hydroxyl-containing bis(alkenyl) ethers when used in a curable sealant composition can improve the compatibility of added fillers. The pendent hydroxyl groups can improve the wettability of the components of the sealant with the surfaces of the filler and can also improve the adhesion of the components to the filler and the dispersion of the filler within the curable sealant composition. In the cured polymer, these attributes can be reflected in enhanced tensile strength, elongation, adhesive strength, and in the case of aerospace sealants, enhanced fuel resistance. Although filler compatibility can be improved by adding wetting or dispersing agents to a curable sealant composition, these additives can reduce the properties of the cured sealant and in particular the properties of the cured sealant following exposure to aviation fluids and/or elevated temperatures.

The presence of the pendent hydroxyl groups can also lead to faster curing of the sealant composition compared to a similar composition using prepolymers without pendent hydroxyl groups. It is believed that the pendent hydroxyl groups result in enhanced hydrogen bonding between adjacent prepolymer chains thereby leading to rapid gelling and subsequent curing. For example, it can be desirable that a curable sealant cure within 10 hours, within 14 hours, or within 18 hours, after the components of a two-part composition are first combined.

EXAMPLES

Embodiments provided by the present disclosure are further illustrated by reference to the following examples, which describe the synthesis, properties, and uses of certain hydroxyl-containing bis(alkenyl) ethers; polythioether prepolymers incorporating hydroxyl-containing bis(alkenyl) ethers in the prepolymer backbone, and compositions comprising hydroxyl-containing bis(alkenyl) ether-containing polythioether prepolymers. It will be apparent to those skilled in the art that many modifications, both to materials, and methods, may be practiced without departing from the scope of the disclosure.

Example 1

Synthesis of Hydroxyl-Containing Bis(Alkenyl) Ether

Sodium hydroxide (108.06 g, 2.70 mol) was added to a flask containing deionized water (360 mL). 1,8-Dimercapto-3,6-dioxaoctane (DMDO) (224.36 g, 1.23 mol) was charged into the solution and the resulting mixture was stirred at 60° C. for 1 to 2 hours. Allyl glycidyl ether (280.33 g, 2.46 mol) was added. The mixture was stirred for 2 to 3 hours. After cooling to room temperature, the mixture was poured into a separation funnel. The top layer was collected and diluted with ethyl acetate. The solution was dried over anhydrous sodium sulfate and then concentrated under reduced pressure to yield 500 g of 4,11,14,21-tetraoxa-8,17-dithiatetracosa-1,23-diene-6,19-diol as a light yellow oil.

Example 2

Synthesis of Hydroxyl-Containing Bsi(Alkenyl) Ether Polythioether Prepolymer 1,8-Dimercapto-3,6-dioxaoctane (DMDO) (167.47 g, 1.83 mol) and triallylcyanurate (TAC) (4.75 g, 0.057 mol) were charged into a flask and heated to 60° C. A mixture of the hydroxyl-containing bis(alkenyl) ether of Example 1 (52.13 g, 0.25 mol; 50% by weight vs DEG-DVE), diethylene glycol divinyl ether (DEG-DVE) (104.25 g, 1.32 mol) and Vazo®-67 (0.16 g) were added to the flask drop-wise. After the catalyst was added the temperature was raised to 70° C. and the mixture was stirred for an several hours until the mercaptan equivalent stopped increasing and no vinyl or allyl peaks were observed in the Fourier transform infrared spectrum (vinyl: ~1618 cm$^{-1}$, 1638 cm$^{-1}$; allyl: ~1644 cm$^{-1}$). The mixture was then stirred at 95° C. for 2 hours and then evacuated at a pressure less than 10 torr at a temperature of 85° C. to 90° C. The resulting 300 g of polythioether prepolymer had a mercaptan equivalent weight of 1511.

Mercaptan equivalent weight was determined using iodine titration according to the following method. A mercaptan-containing material is placed in a 200 mL container.

For mercaptan-terminated monomers 0.05 g is used; for mercaptan-terminated prepolymers from 0.3 g to 0.4 g is used; and for compounds that are not mercaptan-terminated, 5 g is used. One-hundred mL of a 1:1 mixture of methyl ethyl ketone and toluene is added to each container. The mixture is stirred with a stirring bar until the mercaptan compound is completely dissolved. Immediately before titration, 1 mL of pyridine is added. A solution of 0.1N aqueous iodine with a concentration known to 1 part in 1000 is slowly added until the first yellow color appears and persists for 30 seconds. The volume of the iodine solution to reach the endpoint is noted. The mercaptan equivalent weight is calculated according the following equation: SH eq={(weight of sample in grams)×1000}/{mL iodine to endpoint) x (normality of iodine solution)}. The number average molecular weight determined by end-group analysis using iodine titration is then calculated based on the theoretical functionality of the mercaptan-containing compound or combination of compounds.

Example 3

Hardness of Sealant During Cure

The polythioether prepolymer of Example 2 (70.59 g, 0.047 mol) was mixed with an accelerator composition S-5304 (19.00 g, 0.049 mol) (see Table 1) using a mixer (Hauschild Speed Mixer, 2300 rpm, 30 s). DABCO 33-LV (0.71 g; available from Air Products & Chemicals, Allentown, Pa., U.S.) was charged to the mixture and mixed well with the mixer. The mixture was poured into a curing pan in a controlled temperature and humidity chamber (25° C., 50RH %). The increasing hardness during cure was monitored using a Type A durometer in accordance with ASTM D2240. The Shore A hardness of the sealant as a function of time after mixing is shown in FIG. 1.

TABLE 1

| Accelerator composition. | |
| --- | --- |
| Composition | Weight, g |
| Adhesion Promoter* | 5.7 |
| Calcium carbonate | 50.4 |
| Plasticizer | 40 |
| Carbon black | 24 |
| Epoxy Resin, DEN ® 431 | 50 |
| Epoxy Resin, Epon ® 828 | 50 |

*Adhesion promoter, as T-1601, is available from PRC-DeSoto International, Inc.

The above ingredients were thoroughly mixed and the mixture maintained at room temperature for 24 hours before mixing with the prepolymer of Example 2.

Comparative Example 4

Hardness of Comparative Sealant During Cure

A thiol-terminated polythioether polymer, Permapol® P-3.1E (39.46 g, 0.025 mol, EW=1605; available from PRC-DeSoto International, Inc.) was mixed with the accelerator composition S-5304 (10.00 g, 0.026 mol) (see Table 1) using a mixer (Hauschild High Speed Mixer, 2300 rpm, 30 sec). DABCO® 33-LV (0.71 g; available from Air Products & Chemicals) was charged to the mixture and mixed. The mixture was poured into a curing pan in a controlled temperature and humidity chamber (25° C., 50RH %). The increasing of hardness during cure was monitored using a Type A durometer in accordance with ASTM D2240. The Shore A hardness of the sealant as a function of time after mixing is shown in FIG. 1.

Example 5

Modulus of Sealant During Cure

Figure 2:
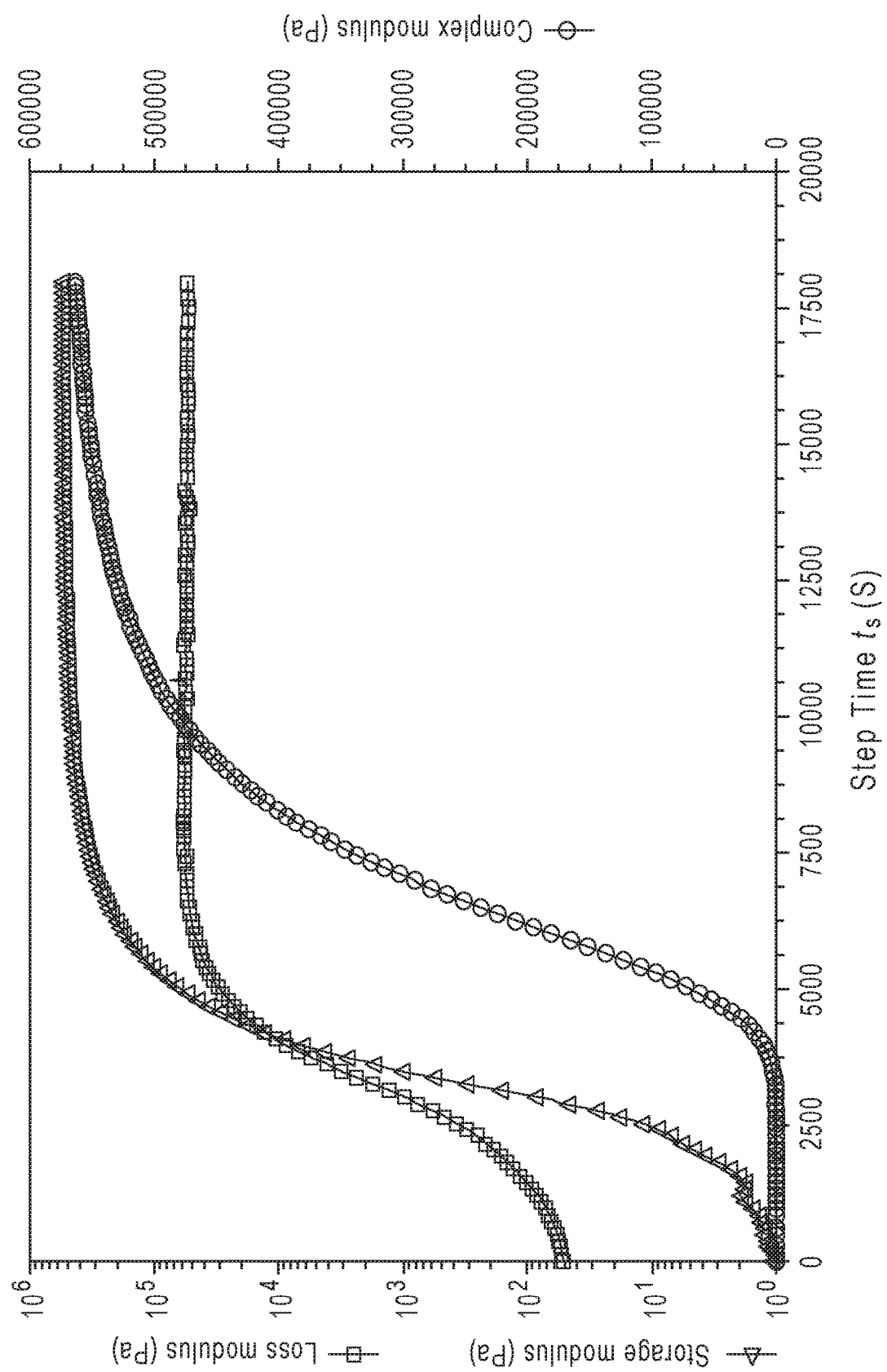
FIG. 2 is a graph showing the complex modulus of sealants during curing.

The sealants of Example 3 and Comparative Example 4 were loaded onto separate plates of a rheometer (TA Discovery Hybrid Rheometer). The complex modulus was recorded over a period of 5 hours. The complex modulus of the sealant as a function of time after mixing is shown in FIG. 2.

Example 6

Tensile and Elongation of Cured Sealant

The compositions of Example 3 and Comparative Example 4 were poured into separate 1/8-inch thick molds and left at room temperature for 2 days. The partially cured sealants were then placed into an oven at a temperature of 140° F. (60° C.) for one day to fully cure. Specimens were cut using Die C as specified in ASTM D412. The tensile strength and % elongation measurements were made at standard conditions in accordance with ASTM D412. The cured composition of Example 3 exhibited a tensile strength of 224±6 psi and an elongation of 256±11%. The composition of Comparative Example 4 exhibited a tensile strength of 219±14 psi and an elongation of 249±18%.

Example 7

Fuel Swell of Cured Sealant

The fuel resistance of cured sealants comprising hydroxyl-containing polythioether prepolymers cured with an epoxy curing agent S-5304 in the presence of an amine catalyst was determined. Hydroxyl-containing polythioether prepolymers were prepared according to Example 2 using DEG-DVE and various hydroxyl-containing divinyl ethers, with different weight ratio. For example, for the hydroxyl-containing polythioether prepolymer used in Composition A in Table 2 the weight of hydroxyl-containing divinyl ether was 20% of the weight of DEG-DVE. Specimens cut from the cured sealant in Example 6 were weighed in air ($W_1$) and in water ($W_2$) and then dried. The specimens were immersed in a minimum of 900 mL of AMS23629 Type I Jet Reference Fluid for 7 days at 140° F. (60° C.) in a closed container. At the end of the exposure period, the closed container was cooled to room temperature. The specimens were removed from the fluid, dipped in methanol (MeOH), and reweighed in air ($W_3$) and water ($W_4$). The specimens were then dried for 24 h at 120° F. (49° C.). The specimens were cooled in a desiccator to standard conditions according to AS5127 and then reweighed ($W_5$).

The percent volume swell was calculated using equation:

$$\text{Percent Swell}=((W_2+W_3)-(W_1+W_4))/(W_1-W_2)\times 100$$

The percent weight loss was calculated using equation:

$$\text{Percent Weight Loss}=(W_1-W_5)/W_1\times 100$$

The results are shown in Table 1.

TABLE 2

Fuel resistance of compositions comprising hydroxyl-containing polythioethers.

| Composition | Hydroxyl-containing Divinyl Ether | Hydroxyl-containing Divinyl Ether content[5] (wt % vs DEG-DVE) | Swell (%) | Weight Loss (%) |
|---|---|---|---|---|
| A | DAE-DMDO[1] | 20 | 19 | 3.9 |
| B | DAE-DMDS[2] | 50 | 17 | 3.6 |
| C | DAE-EDT[3] | 50 | 17 | 3.8 |
| D | DAE-DMDO[1] | 50 | 16 | 4.2 |
| E | DAE-BMEE[4] | 50 | 17 | 4.2 |
| F | none | 0 | 17 | 4.5 |

[1]4,11,14,21-tetraoxa-8,17-dithiatetracosa-1,23-diene-6,19-diol; Formula (2b).
[2]4,18-dioxa-8,11,14-trithiahenicosa-1,20-diene-6,16-diol; Formula (2c).
[3]4,15-dioxa-8,11-dithiaoctadeca-1,17-diene-6,13-diol; Formula (2e).
[4]11,18-trioxa-8,14-dithiahenicosa-1,20-diene-6,16-diol; Formula (2d).
[5]Wt % of total divinyl ether content; hydroxyl-containing divinyl ether and DEG-DVE.

Aspects of the invention are provided as follows:

Aspect 1. A hydroxyl-containing bis(alkenyl) ether of Formula (2):

$$CH_2=CH-(CH_2)_n-O-(CH_2)_n-CH(-OH)-CH_2-S-R^4-S-CH_2-CH(-OH)-(CH_2)_n-O-(CH_2)_n-CH=CH_2 \quad (2)$$

wherein,
each n is independently an integer from 1 to 4; and
$R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-X-]_q-(-CH_2-)_r-$, wherein,
each X is independently selected from $-O-$, $-S-$, and $-S-S-$;
each p is independently an integer ranging from 2 to 6;
q is an integer from 1 to 5; and
r is an integer from 2 to 6.

Aspect 2. The hydroxyl-containing bis(alkenyl) ether of aspect 1, wherein,
each n is 1; and
$R^4$ comprises $C_{2-6}$ n-alkanediyl or $-[(-CH_2-)_p-X-]_q-(-CH_2-)_r-$, wherein,
each X is independently selected from $-O-$ and $-S-$;
each p is 2;
q is an integer from 1 to 5; and
r is 2.

Aspect 3. A hydroxyl-containing bis(alkenyl) ether comprising reaction products of reactants comprising:
(a) a polythiol comprising a dithiol of Formula (6):

$$HS-R^4-SH \quad (6)$$

wherein $R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-X-]_q-(-CH_2-)_r-$, wherein,
each X is independently selected from $-O-$, $-S-$, and $-S-S-$;
each p is independently an integer from 2 to 6;
q is an integer from 1 to 5; and
r is an integer from 2 to 6; and
(b) a compound of Formula (8):

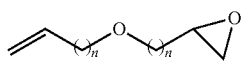

(8)

wherein each n is independently an integer from 1 to 4.

Aspect 4. The hydroxyl-containing bis(alkenyl) ether of aspect 3, wherein the dithiol of Formula (6) comprises a dithiol of Formula (6a), Formula (6b), Formula (6c), Formula (6d), or a combination of any of the foregoing:

$$HS-(CH_2)_2-O-(CH_2)_2-O-(CH_2)_2-SH \quad (6a)$$

$$HS-(CH_2)_2-S-(CH_2)_2-SH \quad (6b)$$

$$HS-(CH_2)_2-O-(CH_2)_2-SH \quad (6c)$$

$$HS-(CH_2)_2-SH \quad (6d)$$

Aspect 5. The hydroxyl-containing bis(alkenyl) ether of any of aspects 3 or 4, wherein, each n is 1; and
$R^4$ comprises $C_{2-6}$ n-alkanediyl or $-[(-CH_2-)_p-X-]_q-(-CH_2-)_r-$, wherein,
each X is independently selected from $-O-$ and $-S-$;
each p is 2;
q is an integer from 1 to 5; and
r is 2.

Aspect 6. A polythioether prepolymer comprising a moiety of Formula (1):

$$-S-R^1-[-S-A-S-R^1-]_s-S- \quad (1)$$

wherein,
s is an integer from 1 to 60;
each A independently comprises a moiety of Formula (2a) or, a moiety of Formula (3a):

$$-(CH_2)_n-O-(CH_2)_n-CH(-OH)-S-R^4-S-CH_2-CH(-OH)-(CH_2)_n-O-(CH_2)^n \quad (2a)$$

$$-(CH_2)_2-O-(R^2-O)_m-(CH_2)_2- \quad (3a)$$

wherein,
each n is independently an integer from 1 to 4;
each $R^1$ comprises $C_{2-10}$ alkanediyl, $C_{6-8}$ cycloalkanediyl, $C_{6-10}$ alkanecycloalkanediyl, or $-[(-CHR-)_p-X-]_q-(CHR)_r-$, wherein each R is independently selected from hydrogen and methyl, wherein,
each X is independently selected from $-O-$ and $-S-$;
each p is independently an integer from 2 to 6;
q is an integer from 1 to 5; and
r is an integer from 2 to 10;
m is 0 to 50; and
each $R^2$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-O-]_q-(-CH_2-)_r-$, wherein,
each p is independently an integer ranging from 2 to 6;
q is an integer from 1 to 5; and
r is an integer from 2 to 10;
$R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-X-]_q-(-CH_2-)_r-$, wherein,
each X is independently selected from $-O-$, $-S-$, and $-S-S-$;
each p is an integer from 2 to 6;
q is an integer from 1 to 5; and
r is an integer from 2 to 6; and
at least one A comprises a moiety of Formula (2a).

Aspect 7. The polythioether prepolymer of aspect 6, wherein from 40 mol % to 60 mol % of the A moieties comprise moieties of Formula (2a).

Aspect 8. The polythioether prepolymer of any of aspects 6 or 7, wherein the polythioether prepolymer comprises:

a difunctional polythioether prepolymer of Formula (1a), a polyfunctional polythioether prepolymer of Formula (1b), or a combination thereof:

$$R^6-S-R^1-[-S-A-S-R^1-]_s-S-R^6 \quad (1a)$$

$$\{R^6-S-R^1-[-S-A-S-R^1-]_s-S-V'-\}_zB \quad (1b)$$

wherein,
each $R^6$ is hydrogen or comprises a moiety comprising a terminal group selected from a thiol, hydroxyl, isocyanate, alkenyl, epoxy, polyalkoxysilyl, and a Michael acceptor;
B comprises a core of a z-valent polyfunctionalizing agent $B(-V)_z$ wherein:
z is an integer from 3 to 6; and
each V is a moiety comprising a terminal group reactive with terminal thiol groups; and
each —V'— is derived from the reaction of —V with a thiol group, or a thiol-terminated polythioether prepolymer of Formula (1c), a thiol-terminated polythioether prepolymer of Formula (1d), or a combination thereof:

$$HS-R^1-[-S-A-S-R^1-]_s-SH \quad (1c)$$

$$\{HS-R^1-[-S-A-S-R^1-]_s-S-V'-\}_zB \quad (1d)$$

wherein,
B comprises a core of a z-valent polyfunctionalizing agent $B(-V)_z$ wherein:
z is an integer from 3 to 6; and
each V is a moiety comprising a terminal group reactive with terminal thiol groups; and
each —V'— is derived from the reaction of —V with a thiol group.

Aspect 9. A polythioether prepolymer comprising reaction products of reactants comprising:
(a) a polythiol comprising a dithiol of Formula (5):

$$HS-R^1-SH \quad (5)$$

wherein,
$R^1$ comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_r-$, wherein:
each p is independently an integer from 2 to 6;
q is an integer from 1 to 5;
r is an integer from 2 to 10;
each R is independently selected from hydrogen and methyl; and
each X is independently selected from —O—, —S—, and —NR$^5$—, wherein R$^5$ is selected from hydrogen and methyl;
(b) a hydroxyl-containing bis(alkenyl) ether of Formula (2):

$$\begin{array}{c}CH_2=CH-(CH_2)_n-O-(CH_2)_n-CH(-OH)-\\CH_2-S-R^4-S-CH_2-CH(-OH)-\\(CH_2)_n-O-(CH_2)_n-CH=CH_2\end{array} \quad (2)$$

wherein,
each n is independently an integer from 1 to 4; and $R^4$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-X-]_q-(-CH_2-)_r-$, wherein,
each X is independently selected from —O—, —S— and —S—S—;
each p is independently an integer from 2 to 6;
q is an integer from 1 to 5; and
r is an integer from 2 to 6; and
(c) a divinyl ether of Formula (3):

$$CH_2=CH-O-(-R^2-O-)_m-CH=CH_2 \quad (3)$$

wherein,
m is 0 to 50; and
each $R^2$ comprises $C_{2-6}$ n-alkanediyl, $C_{3-6}$ branched alkanediyl, $C_{6-8}$ cycloalkanediyl, $C_{6-10}$ alkanecycloalkanediyl, or $-[(-CH_2-)_p-O-]_q-(-CH_2-)_r-$, wherein,
each p is independently an integer ranging from 2 to 6;
q is an integer from 1 to 5; and
r is an integer from 2 to 10.

Aspect 10. The polythioether prepolymer of aspect 9, wherein the polythiol further comprises a polythiol of Formula (7):

$$B(-V)_z \quad (7)$$

wherein,
B comprises a core of a z-valent polyfunctionalizing agent $B(-V)_z$;
z is an integer from 3 to 6; and
each —V is independently a moiety comprising a terminal thiol group or a terminal alkenyl group.

Aspect 11. A composition comprising the hydroxyl-containing bis(alkenyl) ether of any of aspects 1-5.

Aspect 12. The composition of aspect 11, further comprising a thiol-terminated sulfur-containing prepolymer.

Aspect 13. A composition comprising the polythioether prepolymer of any of aspects 6-10.

Aspect 14. A part sealed with the composition of any of aspects 11-13.

Aspect 15. A method of sealing a part, comprising: applying the composition of any of aspects 11 to 13 to a part; and curing the applied composition to seal the part.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled to their full scope and equivalents thereof.

What is claimed is:

1. A polythioether prepolymer comprising reaction products of reactants comprising:
(a) a polythiol comprising a dithiol of Formula (5):

$$HS-R^1-SH \quad (5)$$

wherein,
$R^1$ comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_r-$, wherein:
each p is independently an integer from 2 to 6;
q is an integer from 1 to 5;
r is an integer from 2 to 10;
each R is independently selected from hydrogen and methyl; and each X is independently selected from —O—, —S—, and —NR⁵—, wherein R⁵ is selected from hydrogen and methyl;
(b) a hydroxyl-containing bis(alkenyl) ether of Formula (2):

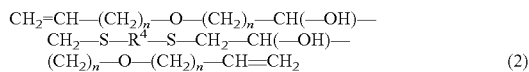

$$CH_2=CH-(CH_2)_n-O-(CH_2)_n-CH(-OH)-CH_2-S-R^4-S-CH_2-CH(-OH)-(CH_2)_n-O-(CH_2)_n-CH=CH_2 \quad (2)$$

wherein,
each n is independently an integer from 1 to 4; and
R⁴ is selected from $C_{2-6}$ n-alkanediyl, $C_{3-6}$ branched alkanediyl, $C_{6-8}$ cycloalkanediyl, $C_{6-10}$ alkanecycloalkanediyl, and —[(—CH₂—)$_p$—X—]$_q$—(—CH₂—)$_r$—, wherein,
each X is independently selected from —O—, —S— and —S—S—;
each p is independently an integer from 2 to 6;
q is an integer from 1 to 5; and
r is an integer from 2 to 6; and
(c) a divinyl ether of Formula (3):

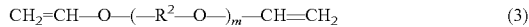

$$CH_2=CH-O-(-R^2-O-)_m-CH=CH_2 \quad (3)$$

wherein,
m is an integer from 0 to 50; and
each R² is selected from $C_{2-6}$ n-alkanediyl, $C_{3-6}$ branched alkanediyl, $C_{6-8}$ cycloalkanediyl, $C_{6-10}$ alkanecycloalkanediyl, and —[(—CH₂—)$_p$—O—]$_q$—(—CH₂—)$_r$—, wherein,
each p is independently an integer from 2 to 6;
q is an integer from 1 to 5; and
r is an integer from 2 to 10.

2. The polythioether prepolymer of claim 1, wherein the reactants further comprise a polyfunctionalizing agent of Formula (7):

$$B(-V)_z \quad (7)$$

wherein,
B comprises a core of a z-valent polyfunctionalizing agent B(—V)$_z$;
z is an integer from 3 to 6; and
each —V is independently a moiety comprising a terminal thiol group or a terminal alkenyl group.

3. The polythioether prepolymer of claim 1, wherein the polyfunctionalizing agent comprises triallyl cyanurate.

4. The polythioether prepolymer of claim 2, wherein,
each n is selected from 1 and 2;
each of R¹ and R⁴ is independently selected from $C_{2-6}$ n-alkanediyl and —[(—CH₂—)$_p$—X—]$_q$—(—CH₂—)$_r$—, wherein,
each X is independently selected from —O— and —S—;
each p is independently selected from 2 and 3;
q is an integer from 1 to 5;
r is selected from 2 and 3;
m is an integer from 0 to 4; and
R² is $C_{2-6}$ n-alkanediyl.

5. The polythioether prepolymer of claim 1, wherein the dithiol of Formula (5) comprises 2,2'-(ethane-1,2-diylbis(oxy))bis(ethane-1-thiol), 2,2'-thiobis(ethane-1-thiol), 2,2'-oxybis(ethane-1-thiol), propane-1,3-dithiol, 2-((2-(2-mercaptoethoxy)ethyl)thio)ethane-1-thiol, or a combination of any of the foregoing.

6. The polythioether prepolymer of claim 1, wherein the hydroxyl-containing bis(alkenyl) ether comprises reaction products of reactants comprising:

(a) a polythiol comprising a dithiol of Formula (6):

$$HS-R^4-SH \quad (6)$$

wherein R⁴ is selected from $C_{2-6}$ n-alkanediyl, $C_{3-6}$ branched alkanediyl, $C_{6-8}$ cycloalkanediyl, $C_{6-10}$ alkanecycloalkanediyl, and —[(—CH₂—)$_p$—X—]$_q$—(—CH₂—)$_r$—, wherein,
each X is independently selected from —O—, —S—, and —S—S—;
each p is independently an integer from 2 to 6;
q is an integer from 1 to 5; and
r is an integer from 2 to 6; and
(b) a compound of Formula (8):

(8)

wherein each n is independently an integer from 1 to 4.

7. The polythioether prepolymer of claim 6, wherein,
the dithiol of Formula (6) comprises 3,6-dioxa-1,8-octanedithiol (DMDO), dimercaptodiethylsulfide (2,2'-thiobis(ethane-1-thiol) (DMDS), 2,2'-oxybis(ethane-1-thiol), 1,2-ethanedithiol, or a combination of any of the foregoing; and
the compound of Formula (8) comprises allyl glycidyl ether.

8. The polythioether prepolymer of claim 1, wherein the hydroxyl-containing bis(alkenyl) ether of Formula (2) comprises 4,11,14,21-tetraoxa-8,17-dithiatetracosa-1,23-diene-6,19-diol; Formula (2b), 4,18-dioxa-8,11,14-trithiahenicosa-1,20-diene-6,16-diol; Formula (2c), 4,15-dioxa-8,11-dithiaoctadeca-1,17-diene-6,13-diol; Formula (2e), 1,18-trioxa-8,14-dithiahenicosa-1,20-diene-6,16-diol; Formula (2d), or a combination of any of the foregoing.

9. The polythioether prepolymer of claim 1, wherein the divinyl ether of Formula (3) comprises divinyl ether, ethylene glycol divinyl ether (EG-DVE), butanediol divinyl ether (BD-DVE), hexanediol divinyl ether (HD-DVE), diethylene glycol divinyl ether (DEG-DVE), triethylene glycol divinyl ether (TEG-DVE), tetraethylene glycol divinyl ether, cyclohexanedimethanol divinyl ether, or a combination of any of the foregoing.

10. The polythioether prepolymer of claim 2, wherein,
the dithiol comprises 1,8-dimercapto-3,6-dioxaoctane (DMDO);
the hydroxyl-containing bis(alkenyl) ether comprises 4,11,14,21-tetraoxa-8,17-dithiatetracosa-1,23-diene-6,19-diol;
the divinyl ether comprises diethylene glycol divinyl ether, triethylene glycol divinyl ether, or a combination thereof; and
the polyfunctionalizing agent comprises triallyl cyanurate.

11. The polythioether prepolymer of claim 1, wherein the reactants comprise:
from 20 mol % to 80 mol % of the hydroxyl-containing bis(alkenyl) ether; and
from 20 mol % to 80 mol % of the divinyl ether,
wherein mol % is based on the total moles of the hydroxyl-containing bis(alkenyl)ether and the divinyl ether.

12. The polythioether prepolymer of claim 1, wherein the reactants comprise:
from 40 mol % to 60 mol % of the hydroxyl-containing bis(alkenyl) ether; and
from 40 mol % to 60 mol % of the divinyl ether, wherein mol % is based on the total moles of the hydroxyl-containing bis(alkenyl)ether and the divinyl ether.

13. The polythioether prepolymer of claim 1, wherein the polythioether prepolymer comprises two or more terminal thiol groups.

14. The polythioether of claim 1 wherein the polythioether prepolymer comprises two or more terminal alkenyl groups.

15. A polythioether prepolymer comprising reaction products of reactants comprising:
the polythioether prepolymer of claim 1; and
a compound comprising a group reactive with a terminal group of the polythioether prepolymer of claim 1, and a reactive functional group.

16. The polythioether prepolymer of claim 15, wherein,
the group reactive with a terminal group of the polythioether prepolymer is selected from a thiol group, an isocyanate group, an alkenyl group, an epoxy group, and a Michael acceptor group; and
the reactive functional group is selected from a hydroxyl group, an isocyanate group, an alkenyl group, an epoxy group, a polyalkoxysilyl group, and a Michael acceptor group.

17. The polythioether prepolymer of claim 15, wherein the polythioether prepolymer comprises at least one terminal group selected from a thiol group, a hydroxyl group, an isocyanate group, an alkenyl group, an epoxy group, a polyalkoxysilyl group, and a Michael acceptor group.

18. The polythioether prepolymer of claim 1, wherein the polythioether prepolymer has an average functionality between 2 and 3.

19. A composition comprising the polythioether prepolymer of claim 1.

20. A cured sealant prepared from the composition of claim 19.

21. A part comprising the cured sealant of claim 20.

22. An aerospace vehicle comprising the cured sealant of claim 20.

23. A method of sealing a surface, comprising:
applying the composition of claim 19 to a surface; and
curing the applied composition to seal the surface.

24. The method of claim 23, wherein the surface comprises a surface of an aerospace vehicle.

25. A composition comprising the polythioether prepolymer of claim 15.

26. A cured sealant prepared from the composition of claim 25.

27. A part comprising the cured sealant of claim 26.

28. An aerospace vehicle comprising the cured sealant of claim 26.

29. A method of sealing a surface, comprising:
applying the composition of claim 25 to a surface; and
curing the applied composition to seal the surface.

30. The method of claim 29, wherein the surface comprises a surface of an aerospace vehicle.

31. A method of making a polythioether prepolymer comprising reacting reactants comprising:
(a) a polythiol comprising a dithiol of Formula (5):

$$HS-R^1-SH \quad (5)$$

wherein,
$R^1$ comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_r-$, wherein:
each p is independently an integer from 2 to 6;
q is an integer from 1 to 5;
r is an integer from 2 to 10;
each R is independently selected from hydrogen and methyl; and
each X is independently selected from $-O-$, $-S-$, and $-NR^5-$, wherein $R^5$ is selected from hydrogen and methyl;
(b) a hydroxyl-containing bis(alkenyl) ether of Formula (2):

$$CH_2=CH-(CH_2)_n-O-(CH_2)_n-CH(-OH)-$$
$$CH_2-S-R^4-S-CH_2-CH(-OH)-$$
$$(CH_2)_n-O-(CH_2)_n-CH=CH_2 \quad (2)$$

wherein,
each n is independently an integer from 1 to 4; and
$R^4$ is selected from $C_{2-6}$ n-alkanediyl, $C_{3-6}$ branched alkanediyl, $C_{6-8}$ cycloalkanediyl, $C_{6-10}$ alkanecycloalkanediyl, and $-[(-CH_2-)_p-X-]_q-(-CH_2-)_r-$, wherein,
each X is independently selected from $-O-$, $-S-$ and $-S-S-$;
each p is independently an integer from 2 to 6;
q is an integer from 1 to 5; and
r is an integer from 2 to 6; and
(c) a divinyl ether of Formula (3):

$$CH_2=CH-O-(-R^2-O-)_m-CH=CH_2 \quad (3)$$

wherein,
m is an integer from 0 to 50; and
each $R^2$ is selected from $C_{2-6}$ n-alkanediyl, $C_{3-6}$ branched alkanediyl, $C_{6-8}$ cycloalkanediyl, $C_{6-10}$ alkanecycloalkanediyl, and $-[(-CH_2-)_p-O-]_q-(-CH_2-)_r-$, wherein,
each p is independently an integer from 2 to 6;
q is an integer from 1 to 5; and
r is an integer from 2 to 10.

32. The method of claim 31, wherein the reactants further comprise a polyfunctionalizing agent of Formula (7):

$$B(-V)_z \quad (7)$$

wherein,
B comprises a core of a z-valent polyfunctionalizing agent $B(-V)_z$;
z is an integer from 3 to 6; and
each $-V$ is independently a moiety comprising a terminal thiol group or a terminal alkenyl group.

33. A method of making a polythioether prepolymer comprising reacting reactants comprising:
the polythioether prepolymer of claim 1; and
a compound comprising a group reactive with a terminal group of the polythioether prepolymer of claim 1, and a reactive functional group.

* * * * *